United States Patent
Tremaglio et al.

(10) Patent No.: US 8,517,921 B2
(45) Date of Patent: Aug. 27, 2013

(54) ENDOSCOPIC INSTRUMENT HAVING REDUCED DIAMETER FLEXIBLE SHAFT

(75) Inventors: Anthony Tremaglio, Charlestown, MA (US); Salvatore Castro, Miford, MA (US)

(73) Assignee: Gyrus ACMI, Inc., Southborough, MA (US)

( * ) Notice: Subject to any disclaimer, the term of this patent is extended or adjusted under 35 U.S.C. 154(b) by 1969 days.

(21) Appl. No.: 11/109,041

(22) Filed: Apr. 18, 2005

(65) Prior Publication Data

US 2005/0250983 A1 Nov. 10, 2005

Related U.S. Application Data

(60) Provisional application No. 60/562,741, filed on Apr. 16, 2004, provisional application No. 60/600,691, filed on Aug. 11, 2004.

(51) Int. Cl.
*A61B 1/00* (2006.01)
*A61B 1/04* (2006.01)

(52) U.S. Cl.
USPC .......................................... 600/128; 600/139

(58) Field of Classification Search
USPC ................. 600/104, 109–110, 121, 123, 129, 600/146, 153, 128
See application file for complete search history.

(56) References Cited

U.S. PATENT DOCUMENTS

| | | | |
|---|---|---|---|
| 3,712,984 A | 1/1973 | Lienhard | |
| 4,198,960 A | * | 4/1980 | Utsugi .......................... 600/104 |
| 4,567,880 A | | 2/1986 | Goodman |
| 4,573,450 A | | 3/1986 | Arakawa |
| 4,602,281 A | | 7/1986 | Nagasaki et al. |
| 4,682,219 A | | 7/1987 | Arakawa |

(Continued)

FOREIGN PATENT DOCUMENTS

| EP | 0027361 | 4/1981 |
|---|---|---|
| EP | 0 355 996 A2 | 2/1990 |

(Continued)

OTHER PUBLICATIONS

Kodak, "Shutter Operations for CCD and CMOS Image Sensors Revision 2.0" Dec. 17, 2003 http://www.kodak.com/global/plugins/acrobat/en/business/ISS/supportdocs/ShutterOperations.pdf—4 pages.

(Continued)

*Primary Examiner* — Philip R Smith
(74) *Attorney, Agent, or Firm* — The Dobrusin Law Firm, P.C.

(57) ABSTRACT

A medical instrument comprising a flexible, filamentous shaft slideably disposed in a sheath, the instrument including an electronic imaging system comprising an image sensor carried on a distal end portion of the instrument. The shaft may be used as a guidewire for a complementary guided device, or it may be used to carry a functional element for performing a procedure at a target site in a patient's body. In other embodiments, the present invention contemplates a flexible sheath, preferably having a simple tubular construction, with an electronic imaging system at its distal end. The sheath is adapted to slideably receive a shaft, preferably a filamentous shaft, that closely fits the sheath. The shaft carries functional element at its distal end. The instruments according to the present invention may include one or more filaments along their length for deflecting an insertable portion of the instrument.

20 Claims, 15 Drawing Sheets

(56) References Cited

U.S. PATENT DOCUMENTS

| | | | |
|---|---|---|---|
| 4,685,449 A | 8/1987 | Bonnet | |
| 4,692,608 A | 9/1987 | Cooper et al. | |
| 4,809,680 A | 3/1989 | Yabe | |
| 4,832,003 A | 5/1989 | Yabe | |
| 4,884,133 A | 11/1989 | Kanno et al. | |
| 4,911,148 A * | 3/1990 | Sosnowski et al. | 600/136 |
| 4,925,445 A | 5/1990 | Sakamoto et al. | |
| 5,040,068 A | 8/1991 | Parulski et al. | |
| 5,178,130 A | 1/1993 | Kaiya | |
| 5,187,572 A | 2/1993 | Nakamura et al. | |
| 5,192,286 A | 3/1993 | Phan et al. | |
| 5,301,061 A | 4/1994 | Nakada et al. | |
| 5,307,803 A * | 5/1994 | Matsuura et al. | 600/140 |
| 5,325,847 A | 7/1994 | Matsuno | |
| 5,402,768 A | 4/1995 | Adair | |
| 5,430,475 A | 7/1995 | Goto et al. | |
| 5,573,493 A | 11/1996 | Sauer et al. | |
| 5,598,205 A | 1/1997 | Nishioka | |
| 5,607,419 A | 3/1997 | Amplatz et al. | |
| 5,607,436 A | 3/1997 | Pratt et al. | |
| 5,704,892 A | 1/1998 | Adair | |
| 5,817,015 A | 10/1998 | Adair | |
| 5,846,183 A | 12/1998 | Chilcoat | |
| 5,850,496 A | 12/1998 | Bellahsene et al. | |
| 5,857,961 A | 1/1999 | Vanden Hoek et al. | |
| 5,863,366 A | 1/1999 | Snow | |
| 5,941,818 A | 8/1999 | Hori et al. | |
| 5,957,834 A | 9/1999 | Mochida | |
| 6,006,119 A | 12/1999 | Soller et al. | |
| 6,124,883 A | 9/2000 | Suzuki et al. | |
| 6,142,930 A | 11/2000 | Ito et al. | |
| 6,184,923 B1 | 2/2001 | Miyazaki | |
| 6,206,825 B1 | 3/2001 | Tsuyuki | |
| 6,240,231 B1 | 5/2001 | Ferrera et al. | |
| 6,352,531 B1 | 3/2002 | O'Conner et al. | |
| 6,414,710 B1 | 7/2002 | Takahashi et al. | |
| 6,428,469 B1 | 8/2002 | Iddan et al. | |
| 6,449,006 B1 | 9/2002 | Shipp | |
| 6,459,919 B1 | 10/2002 | Lys et al. | |
| 6,471,684 B2 | 10/2002 | Dulak et al. | |
| 6,547,721 B1 | 4/2003 | Higuma et al. | |
| 6,579,224 B1 | 6/2003 | Burton et al. | |
| 6,579,277 B1 | 6/2003 | Rabiner et al. | |
| 6,648,874 B2 | 11/2003 | Parisi et al. | |
| 6,659,940 B2 | 12/2003 | Adler | |
| 6,692,430 B2 | 2/2004 | Adler | |
| 6,702,972 B1 | 3/2004 | Markle | |
| 6,976,956 B2 | 12/2005 | Takahashi et al. | |
| 6,994,667 B2 | 2/2006 | Singh | |
| 7,030,904 B2 | 4/2006 | Adair et al. | |
| 7,101,379 B2 | 9/2006 | Gregory, Jr et al. | |
| 7,207,980 B2 | 4/2007 | Christian et al. | |
| 7,214,183 B2 * | 5/2007 | Miyake | 600/131 |
| 7,241,262 B2 | 7/2007 | Adler et al. | |
| 7,300,397 B2 | 11/2007 | Adler et al. | |
| 7,559,892 B2 | 7/2009 | Adler et al. | |
| 7,591,783 B2 | 9/2009 | Boulais et al. | |
| 2001/0026666 A1 | 10/2001 | Ferrera et al. | |
| 2001/0031912 A1 | 10/2001 | Adler | |
| 2001/0040211 A1 | 11/2001 | Nagaoka | |
| 2001/0044571 A1 * | 11/2001 | Mitsumori | 600/167 |
| 2002/0013512 A1 | 1/2002 | Sendai et al. | |
| 2002/0095066 A1 | 7/2002 | Kamrava | |
| 2002/0154215 A1 | 10/2002 | Schechterman et al. | |
| 2002/0177750 A1 | 11/2002 | Pilvisto | |
| 2002/0188175 A1 * | 12/2002 | Levine et al. | 600/159 |
| 2003/0009086 A1 | 1/2003 | Black et al. | |
| 2003/0088254 A1 * | 5/2003 | Gregory et al. | 606/127 |
| 2003/0142753 A1 | 7/2003 | Gunday | |
| 2004/0034311 A1 | 2/2004 | Mihalcik | |
| 2004/0039250 A1 * | 2/2004 | Tholfsen et al. | 600/104 |
| 2004/0111012 A1 * | 6/2004 | Whitman | 600/179 |
| 2004/0133075 A1 * | 7/2004 | Motoki et al. | 600/131 |
| 2004/0140425 A1 | 7/2004 | Iizuka et al. | |
| 2004/0193140 A1 | 9/2004 | Griffin et al. | |
| 2004/0230097 A1 * | 11/2004 | Stefanchik et al. | 600/127 |
| 2004/0242962 A1 | 12/2004 | Uchiyama | |
| 2004/0249246 A1 | 12/2004 | Campos | |
| 2005/0075538 A1 * | 4/2005 | Banik et al. | 600/141 |
| 2005/0080342 A1 * | 4/2005 | Gilreath et al. | 600/476 |
| 2005/0096502 A1 * | 5/2005 | Khalili | 600/106 |
| 2005/0228361 A1 | 10/2005 | Tremaglio | |
| 2005/0267328 A1 | 12/2005 | Blumzvig et al. | |
| 2005/0277810 A1 | 12/2005 | Irion | |
| 2006/0055793 A1 | 3/2006 | Adler et al. | |
| 2006/0173242 A1 | 8/2006 | Navok et al. | |
| 2006/0183976 A1 | 8/2006 | Adler et al. | |
| 2007/0177009 A1 | 8/2007 | Bayer et al. | |
| 2007/0185386 A1 | 8/2007 | Cheng | |
| 2007/0215268 A1 | 9/2007 | Pingleton et al. | |
| 2007/0276182 A1 | 11/2007 | Adler et al. | |
| 2008/0033423 A1 | 2/2008 | Peacock, III | |
| 2008/0114303 A1 | 5/2008 | Tremaglio | |
| 2008/0183043 A1 | 7/2008 | Spinnler et al. | |
| 2009/0036744 A1 | 2/2009 | Vayser | |

FOREIGN PATENT DOCUMENTS

| | | |
|---|---|---|
| EP | 0 355 996 A3 | 2/1990 |
| EP | 0647425 A1 | 4/1995 |
| EP | 0 573 746 B1 | 12/1995 |
| EP | 1 202 767 B1 | 7/2000 |
| JP | 60104915 | 6/1985 |
| JP | 60258515 | 12/1985 |
| JP | 62-35314 | 3/1987 |
| JP | 04236934 | 8/1992 |
| JP | 08024219 | 1/1996 |
| JP | 08114755 | 5/1996 |
| JP | 2000139821 | 5/2000 |
| JP | 2002508201 | 3/2002 |
| WO | WO9930610 | 6/1999 |
| WO | WO0176452 | 10/2001 |
| WO | 02/078632 A2 | 10/2002 |
| WO | WO03013624 | 2/2003 |
| WO | WO 03/028547 A2 | 4/2003 |
| WO | WO 03/098913 A2 | 11/2003 |
| WO | WO03098913 | 11/2003 |
| WO | WO2005072806 | 8/2005 |
| WO | WO2006032013 | 3/2006 |
| WO | WO2007134341 | 11/2007 |
| WO | WO2007137184 | 11/2007 |

OTHER PUBLICATIONS

Non-Final Office Action dated Jun. 27, 2006 from related U.S. Appl. No. 11/105,808; 7 pages.

Final Office Action dated Dec. 20, 2006 from related U.S. Appl. No. 11/105,808; 7 pages.

Decision on Appeal dated Jun. 25, 2010 from related U.S. Appl. No. 11/105,808; 8 pages.

Japanese Office Action dated Mar. 18, 2009, for corresponding Japanese patent application No. 2004-506277; Informal English translation provided by Japanese agent; 4 pages.

Japanese Office Action dated Dec. 22, 2009, for a related Japanese Patent Application No. 2004-506277; 11 pages. Informal English translation from the Japanese agent is included.

Non-Final Office Action dated Jul. 22, 2009 from related U.S. Appl. No. 10/514,607; 11 pages.

Non-Final Office Action dated Nov. 24, 2009 from related U.S. Appl. No. 10/514,607; 10 pages.

Final Office Action dated May 28, 2010 from related U.S. Appl. No. 10/514,607; 12 pages.

Examination Report from the German Patent and Trademark Office dated Jul. 12, 2010 for related German patent application No. 102008018931.6; informal English translation provided by German agent is included; 10 pages total.

PCT International Search Report and Written Opinion dated Sep. 27, 2010 for related patent application No. PCT/US2010/040100, filed Jun. 25, 2010; 13 pages.

* cited by examiner

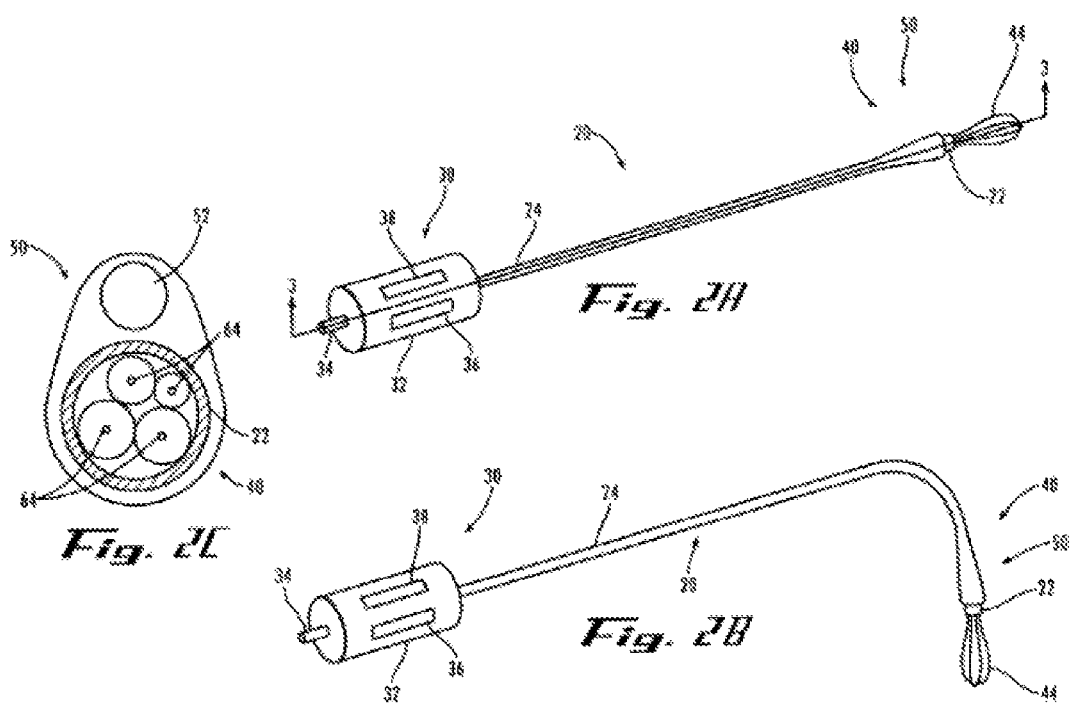

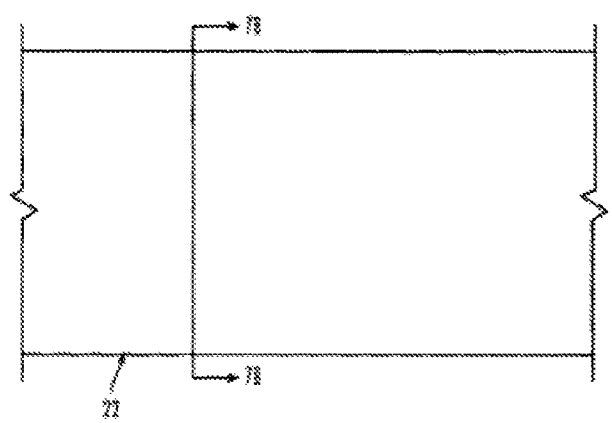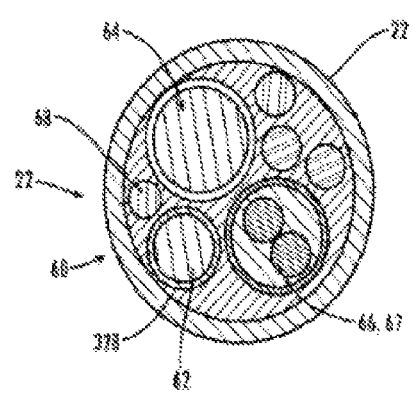

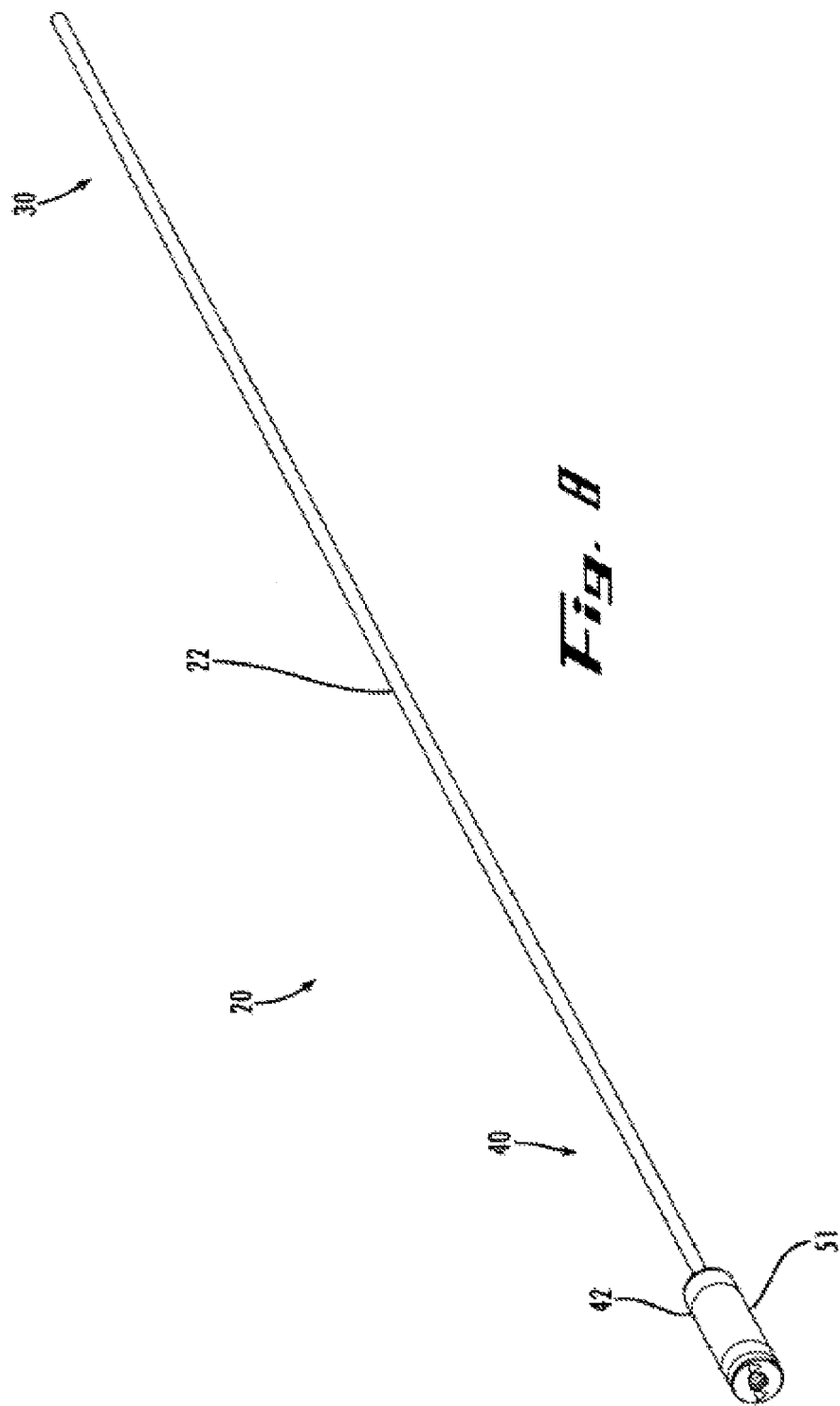

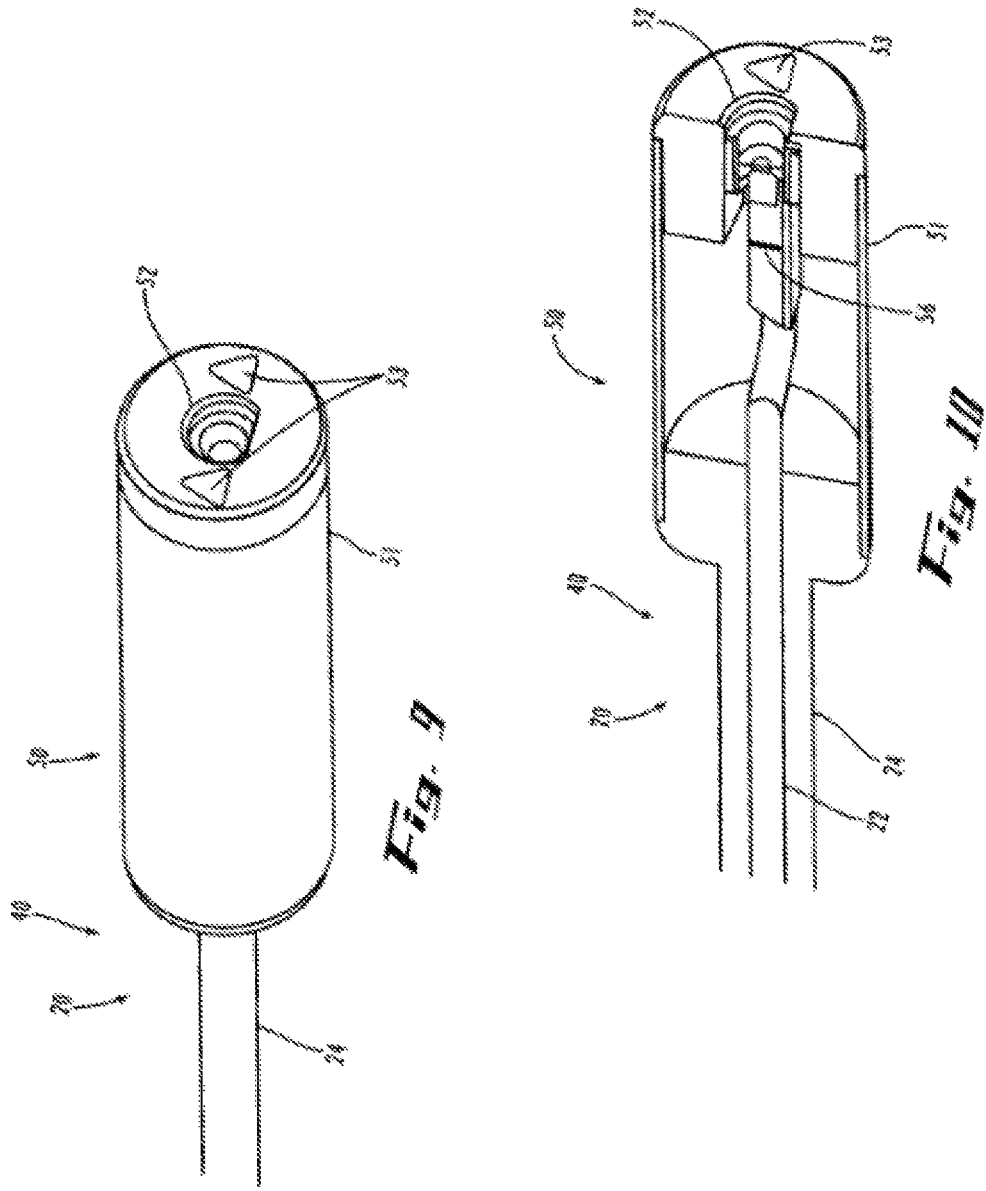

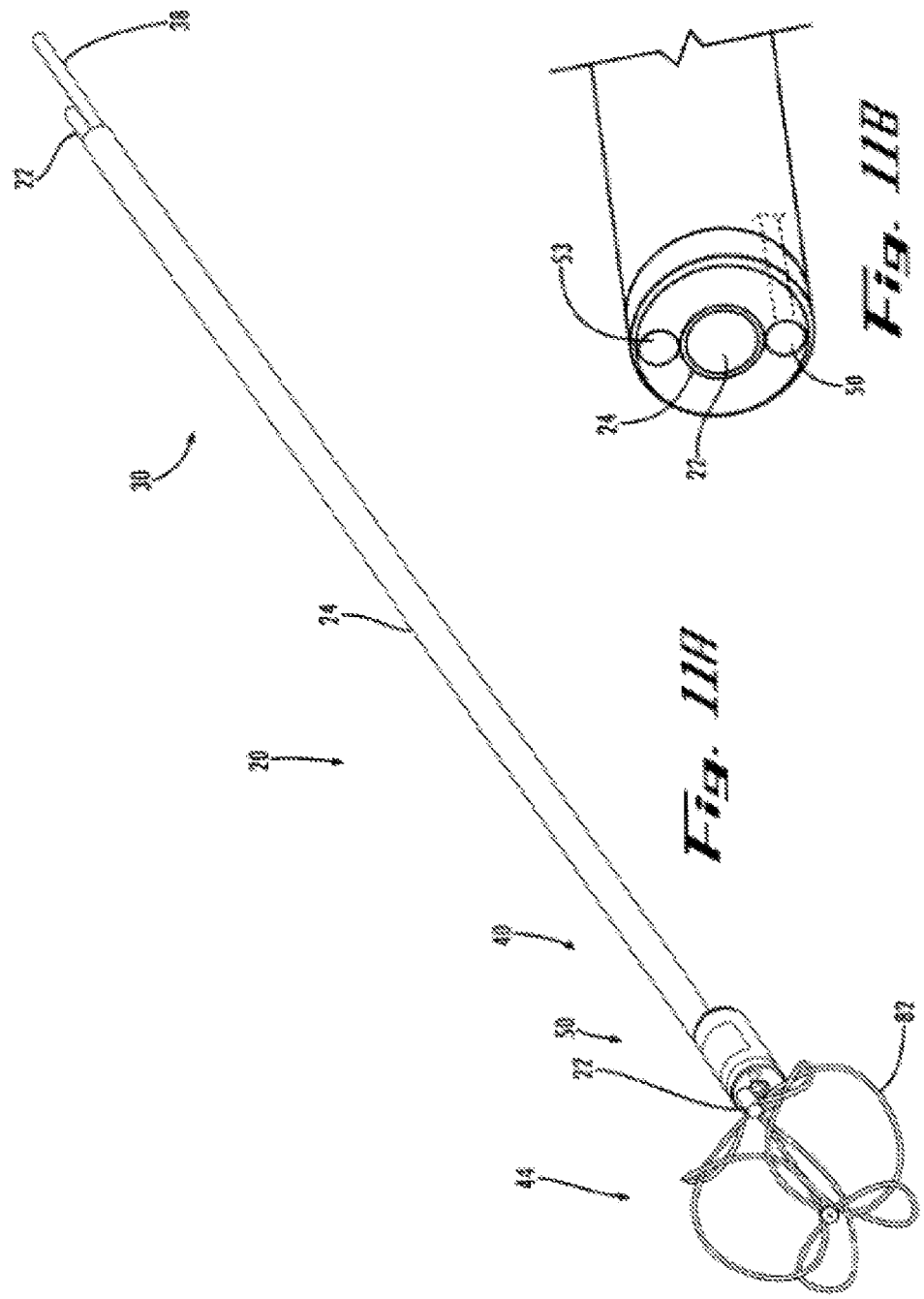

ENDOSCOPIC INSTRUMENT HAVING REDUCED DIAMETER FLEXIBLE SHAFT

RELATED APPLICATIONS

This application claims priority from U.S. Provisional Patent Application Ser. No. 60/562,741, titled "RETRIEVAL DEVICE WITH OR WITHOUT CHIP TECHNOLOGY," filed Apr. 16, 2004; and from U.S. Provisional Patent Application Ser. No. 60/600,691, titled "GUIDEWIRE ENDOSCOPE," filed Aug. 11, 2004; the contents of which are hereby incorporated by reference as if recited in full herein for all purposes.

BACKGROUND OF THE INVENTION

The present invention relates to medical instruments and devices; and in particular to endoscopes, guidewires, retrieval devices, and similar tools often used alone or in combination for minimally invasive medical procedures.

An endoscope is a medical instrument used to inspect the inside of the body. A typical endoscope has a distal end comprising an optical or electronic imaging system, a proximal end with controls for manipulating the endoscope, a rigid or flexible tubular, elongate shaft connecting the ends, and a steering means to control the deflection of the distal end. Often, the steering mechanism includes a complicated set of mechanical linkages within the shaft. To use an endoscope, the physician inserts the distal end into the patient through a natural orifice or an artificial incision, pushes the shaft into the patient, monitors the progress of the distal end inside the patient by watching the acquired image, and controls the angle of view and the direction of progress by the steering mechanism in order to maneuver the distal end to the site of interest. The proximal end remains outside the patient, where it is connected to an eyepiece, video monitor, or other equipment, for example, to display the acquired image.

Some endoscopes are inspection devices not used for remote procedures. Other endoscopes let a physician, surgeon, or medical technician pass tools or treatments through a lumen, called a "working channel," that runs lengthwise within the endoscope shaft. The physician often uses the working channel to tools or other instruments, called "functional elements," into the patient, for example, to perform endoscopic surgical procedures. A tool often used in conjunction with an endoscope is a retrieval device, typically used to capture and extract objects, such as stones or foreign bodies, or to resect and extract tissue, such as polyps or biopsy samples. A typical retrieval device comprises a distal end having a retrieval basket formed from one or more wire loops and a proximally extending shaft having a filamentous construction of one or more bundled wires. The basket and shaft may be slideably disposed in a sheath, which is usually a thin-walled, flexible polymer tube. Typically, the basket is resiliently collapsible as its shaft is drawn proximally into its sheath via a slide actuator in a handle at the proximal end.

To use a retrieval device, the physician first inserts a general-purpose endoscope into the patient and guides it to the site of interest. The physician then inserts the distal end of the retrieval device into the proximal end of the working channel and pushes the retrieval device down the channel until it emerges from the distal end, so that the distal end of the retrieval device becomes visible through the endoscope. The physician can then watch the endoscope image of the retrieval device in order to guide the device to the object of interest; maneuver the open basket to surround the object; collapse the basket via the slide actuator to trap the object; and withdraw the device back up the working channel to extract the object from the patient. Because the retrieval device does not provide for image acquisition or for guiding the device to a target site within the patient's body, the procedure requires two major components: an endoscope (for steering and imaging) and a retrieval device (for guiding and extracting).

Another medical instrument, sometimes used with an endoscope but also used independently, is a guidewire. In essence, a guidewire is a filament or group of filaments inserted into to the body, typically to facilitate emplacement of a medical device. For example, the physician inserts the guidewire through a natural orifice or an artificial incision, advances the guidewire to a site of interest, slips a catheter (for example) over the guidewire, advances the catheter over the guidewire, and then withdraws the guidewire, leaving the catheter in place. To gauge the location of a conventional guidewire within the body, the physician relies on feel, fluoroscopy, or endoscopic imaging. To aid in manipulating the guidewire, the physician may grasp it with a torque handle or similar device, which is removable to facilitate passing the catheter (for example) over the guidewire.

Using a general-purpose endoscope as a "host" to insert a second, specialized tool such as a guidewire or a retrieval device creates a complex system with several drawbacks. One problem with the conventional approach is that general-purpose endoscopes are expensive instruments with relatively short lifetimes and high maintenance costs. Using a general-purpose endoscope for specialized, recurring tasks exposes it to wear and tear, for example, during cleaning, sterilization, handling, and use.

A second problem relates to the ongoing goal of reducing the diameter of endoscopic surgical instruments. A major benefit of endoscopic surgery is that an endoscopic procedure is usually far less invasive than its traditional surgical alternative. That said, inserting an endoscope and guiding it to the site of interest can be an uncomfortable and upsetting experience for the patient. Cystoscopy, for example, is a procedure for inspecting of the interior of the bladder. A physician may perform cystoscopy in an office setting with the patient awake. The physician typically gives the patent a local anesthetic and then inserts a type of endoscope called a cystoscope up the patient's urethra and into the bladder. For the patient, this procedure can be physically and mentally uncomfortable. The amount of discomfort depends on, among other things, the diameter of the cystoscope. Existing cystoscopes have a diameter of about 16 French—which is more than 5 mm. Reducing this diameter would improve patient comfort by reducing the amount of urethral dilation during cystoscopy.

The benefits of smaller-diameter endoscopic instruments generalize from cystoscopes to endoscopic instruments as a class. In addition to reducing discomfort, smaller endoscopic instruments also reduce the invasiveness of endoscopic procedures, especially for those requiring an artificial incision. A smaller instrument requires a smaller incision, contributing to faster recovery, reduced scarring, and a lower risk of complications—and therefore to a lower average cost per procedure. Smaller instruments also extend the range of procedures that can be accomplished endoscopically, enhancing the utility of endoscopic instruments and reducing the need for conventional surgery. Smaller diameter endoscopic instruments are always a welcome addition to the art.

SUMMARY OF THE INVENTION

The present invention overcomes the disadvantages of the prior art by providing instruments that are less traumatic and less invasive due to their small size and flexibility; simpler and less expensive to construct; easier to use and more effective; and optionally are disposable due to their simplicity and relative inexpensiveness. More particularly, the present invention overcomes problems in the prior art by providing a medical instrument with the following characteristics, alone or in combination:

In certain aspects, the present invention relates to instruments or devices for minimally invasive medical procedures. In certain embodiments, the present invention provides novel endoscopic instruments or devices that comprise a filamentous shaft that supports an imaging system at the distal end of the shaft or thereabouts. The filamentous shaft comprises one or more filaments that carry an electronic imaging system. Optionally, the shaft may include filaments, such as pull wires to control deflection (which controls viewing direction within the body and the serves as a means for steering); pull wires to control functional elements; conductors for power and signals to the imaging and illumination systems; conductors such as fiber optics to carry light; and filaments to modify physical properties such as stiffness. In some embodiments, the various filaments form a filamentous core. In some embodiments, a jacket may surround or encapsulate the core to hold the filaments together as a coherent functional unit. In some embodiments, the shaft or jacketed shaft may be disposed within a sheath, which is an outer covering surrounding the shaft. The shaft or jacketed shaft may be slideably disposed within the sheath. When present, the sheath may be a relatively thin-walled, tube-like covering formed from (for example) extruded polymer; or it may be tube-like structure that carries one or more filaments in the sheath wall; or it may be a flexible filament helically wrapped over the core to bundle the filaments together; or it may be a flexible rod encapsulating the filaments and filling the interstices among them.

At the distal end, these filamentous structures support an electronic imaging system adapted to acquire an image in a restricted space, such as an internal body cavity or interstitial space. In certain preferred embodiments, this imaging system—which is essentially a small video camera—is based on a pixilated image sensor such as a Charge Coupled Device (CCD), a Complementary Metal Oxide Semiconductor (CMOS) image sensor, or on a similar analog or digital sensor disposed at or near the distal end of the shaft or sheath constructions. The imaging system typically further comprises one or more optical elements for transmitting an image to the active surface of the image sensor. Such elements may include a protective optical window; objective optics to focus the image on the sensor; and one or more prisms or mirrors to redirect the optical axis by a predetermined angle; alone or in any combination. The imaging system typically further comprises supporting electronics and conductors, for example, to interpret control signals and to transmit image signals to onboard or external equipment.

The filamentous shaft may also carry an illumination system to provide light for the imaging system. (As used herein "carry", and its variants, means "disposed on the inside or outside the stated object.") The illumination system, for example, may be one or more LEDs or other solid-state lights that transmit light to a target site in the patient's body. The LEDs can be disposed at the distal end of the shaft or sheath and connected to a power source in the instrument (such as a battery) or outside of it (by way of a power conductor). The LEDs may also be located elsewhere and deliver their light by one or more optical fibers that are carried on the shaft.

The combination of the shaft and imaging system provides a narrow diameter (or small French) structural connection plus electrical conductors that minimizes its diameter compared to other medical devices such as traditional endoscopes, which have complicated tubular housing with mechanical linkages and/or optical trains or fibers for conveying an image proximally outside the patient's body. In essence, adding imaging (and possibly steering) to a guidewire-like filamentous shaft effectively eliminates the need for a general-purpose, tubular endoscope in certain medical contexts, and therefore reduces the diameter of the instrument imposed on the patient during the procedure.

A filamentous shaft offers the advantage of easily serving as a base for functional or accessory elements (such as those described below). The filaments that comprise the shaft may be constructed from any material, or combination of materials, that provides the characteristics suitable for use as a medical device, such as aluminum, stainless steel, Nitinol, copper, and other metals or alloys thereof; plastic, carbon fiber, fiberglass, polypropylene, and other polymers; or any combination thereof. A filament, or a group of filaments, may be encased in a sleeve, for example, to provide protection, electrical insulation, or to create a slideably passageway for the sleeved filament or group of filaments.

Where a plurality of filaments are used, they may be arranged in bundles, intertwined, encapsulated in a jacket, wrapped with other filaments, or in other known arrangements. The several filaments may have the same or different properties. For example, one or more filaments may be larger to provide more rigidity than surrounding filaments. One or more filaments may serve as power conductors, signal conductors, or both for the imaging system, illumination system, or both. Similarly, any given filament may have properties that vary along its length, and such variations may differ among various filaments. For example, the distal portion of a filament may be less rigid than the proximal portion to achieve a desired balance of pushability and steerability in the instrument. This balance is an important consideration in the design of instruments used in tight and tortuous passages.

In certain embodiments, the present invention provides novel combinations of a filamentous shaft, a means for deflecting (steering) the shaft within the patient, and an electronic imaging system. Such embodiments may serve as a self-contained, video-guided instrument that may be used independently from a traditional endoscope.

The filamentous shafts with imaging systems of the present invention may be adapted for use as a guidewire. Because an endoscopic guidewire according to the present invention has an integral means for acquiring an image and may have an integral means for deflecting (steering) the distal end, the physician can guide it to the site of interest within the patient's body without relying on feel, fluoroscopy, or a general-purpose endoscope. In certain embodiments, the handle portion of an endoscopic guidewire according to the present invention is omitted, removable, or otherwise configured to aid in passing a device such as a catheter over the filamentous shaft.

In other embodiments, the present invention further comprises a functional element supported by the filamentous shaft or sheath and located at the distal end of the shaft or sheath or thereabouts. Functional elements include various devices for performing procedures on an object or tissue at a target site in the patient's body. For example, the functional element may be used for grasping or retrieving objects such as foreign bodies or stones (calculi) from the patient's body; or it may be used for cutting and retrieving polyps or biopsy samples. Contemplated functional element devices include retrieval baskets, biopsy forceps, suction devices, electrosurgical devices, laser devices, and ablation devices.

Because endoscopic devices with a functional element according to the present invention provide for image acquisition and may provide for deflection within the body, such devices do not require a separate, general-purpose endoscope. In certain embodiments, the present invention therefore represents an "all in one" solution to medical tasks that conventionally require two or more tools, namely a general-purpose endoscope (for imaging and steering) plus one or more accessory tools to perform the actual procedure (for example, a retrieval device to capture an object or tissue sample). Eliminating the "host" endoscope reduces the diameter of the instrument impinged on the patient.

In certain embodiments, the present invention also provides sheaths in which a filamentous shaft (or a jacketed filamentous shaft) may be slideably disposed. The sheaths may be used with the filamentous shafts of the present invention. And they may be used to carry the imaging system or illumination system for an assembly of shaft and sheath.

In a possible embodiment, the present invention contemplates a medical instrument comprising a flexible, filamentous shaft slideably housed in a flexible sheath, the instrument including an image sensor carried on a distal end portion of the instrument. The insertable portion of the sheath may comprise a flexible polymer tube. The instrument may include a functional element disposed on the distal end of the shaft. The functional element may have a first configuration for being carried in the sheath and a second configuration when deployed from the distal end of the sheath. The functional element may comprise a device for capturing an object or manipulating tissue at a target site in a patient's body. In the instrument, at least one filament may be carried along a length of the instrument and is operatively coupled to the instrument so as to allow a user to control the deflection of at least a distal portion of the instrument. In the instrument, a filament may be slideably disposed in a channel along at least a portion of the length of the sheath. The instrument may include at least one pullable filament that has a distal portion operatively coupled to a distal end portion of the instrument and a proximal end portion operatively coupled to a tension mechanism at the proximal end of the instrument, the tension mechanism being controllable by a user to cause a distal end of the instrument to deflect. The tension mechanism may include a slide mechanism disposed on the handle of the instrument. The instrument may include at least one solid-state illumination source, such as an LED, carried at the distal end of the instrument on the shaft and/or the sheath. Advantageously, by placing, for example, the light source on the shaft and the imaging system on or in the sheath more reduction in diameter is possible compared to placing both imaging system and light source on the sheath or the shaft. Accordingly, the solid state light source may be carried on the shaft or the sheath, and the image sensor is carried on whichever of the shaft and sheath the light source is not carried.

There present invention also contemplates a medical instrument comprising a flexible, filamentous shaft, the instrument including an imaging system comprising a pixellated image sensor carried on a distal end portion. The shaft may comprise a guidewire capable of receiving a predetermined guided device, the shaft and guidewire forming a functionally complementary assembly so as to enable delivery or placement of the guided device in desired location in a patient's body. The guidewire may be included in an assembly of guidewire and guided device. The guided device may be, for example, a catheter or stent. The shaft may have a proximal portion with a first set of predetermined properties and a distal portion with a second set of predetermined properties, the first set of properties aimed at providing pushability for the shaft and the second set aimed at providing steerability for the instrument so as to facilitate the delivery of an insertable portion of the instrument to a desired target site in a patient's body. In this and other embodiments of the present invention the image sensor may be a CMOS image sensor; the image sensor may have an active an imaging surface (i.e., pixel array or other array of photosensitive areas) oriented non-perpendicularly to the optical axis of the shaft; and the image sensor may have an active imaging surface that is longer than the inner diameter of a sheath or housing for the image sensor.

In certain embodiments, the shaft comprises between 2-5 filaments, at least one filament providing structural support of predetermined rigidity and flexibility and at least one filament operatively coupled to the image sensor and comprising an electrical conduit for power and/or signals.

The present invention also contemplates a medical instrument device, comprising: a flexible sheath adapted to slideably receive a flexible, filamentous shaft having a functional element at the distal end for performing a procedure on an object or tissue at a target site in a patient's body; a deflection system comprising at least one filament with a distal end portion operatively coupled to a distal end portion of the instrument and proximal end operatively coupled to a proximal end portion of the instrument, and a control mechanism at the proximal end portion of the instrument enabling a user to pull the filament and deflect the distal end portion; and an imaging system comprising an image sensor carried on a distal portion of the instrument. In this and other embodiments the sheath is thin-walled a polymer tube that provides for simple and inexpensive construction. Such a tube may be selected so as not to interfere with the pushability and steerability of a shaft. The tube may be selected to have a substantially uniform composition along a majority of the insertable, distal portion. To minimize instrument diameter, in an the assembly of the sheath and shaft, the shaft may have an outer diameter that closely matches the inner diameter of the sheath so that overall outer diameter of the instrument is minimized.

The present invention also contemplates a medical instrument device, comprising: a flexible sheath comprising a polymer tube that is adapted to slideably receive a flexible, filamentous shaft having a functional element at the distal end for performing a procedure on an object or tissue at a target site in a patient's body; a deflection system comprising at least one filament with a distal end portion coupled to a distal end portion of the instrument and proximal end portion coupled to a proximal end portion of the instrument, and a control mechanism at the proximal end portion of the instrument enabling a user to manipulate the filament and deflect the distal end portion of the instrument; and the shaft has an outer diameter that closely matches the inner diameter of the sheath so that overall outer diameter of the instrument is minimized.

The present invention also contemplates a medical instrument comprising a flexible, filamentous shaft slideably housed in a flexible sheath, the instrument including an image sensor carried on a distal end portion of the shaft, the shaft including one or more filaments constructed and arranged to provide pushability and steerability to the instrument sufficient to deliver the distal end of the instrument to a predetermined target site in a patient's body, the shaft including one or more conductors operatively coupled to the image sensor so as to communicate power and signals between the sensor and a location proximal to the insertable portion of the instrument. In this and other embodiments, the instrument comprises a guidewire capable of receiving a predetermined guided device, the shaft and guidewire forming a functionally complementary assembly so as to enable delivery of the guided device to a target location in a patient's body.

The instruments according to the present invention may be used to deliver the guided device, such as a catheter or stent to a region comprising the ureter, bladder or kidney, or to a region comprising the esophageal tract or gastrointestinal tract of a patient, as well as any other region.

The shaft of the present invention may include a plurality of filaments, one filament being disposed in a sleeve. The may be an electrical insulator and the filament it encases a conduit for communication of power and/or electrical signals between proximal and distal ends of the instrument. The sleeve may also hold slideable wire that controls deflection of the shaft or operation of a functional element on the shaft. The foregoing features and embodiments may be used in various combinations, as persons skilled in the art will appreciate from the teachings herein.

The foregoing is not intended to be an exhaustive list of embodiments and features of the present invention. Persons skilled in the art are capable of appreciating other embodiments and features from the following detailed description in conjunction with the drawings.

BRIEF DESCRIPTION OF THE DRAWINGS

FIGS. 1 through 17 show representative embodiments of the present invention, wherein similar features share common reference numerals.

FIG. 2A shows a side view of another embodiment of an endoscopic instrument according to the present invention, further comprising a representative functional element—in this case, a retrieval basket;

FIG. 2B shows a side view of the embodiment of FIG. 2A in a deflected configuration;

FIG. 2C shows an end view of the embodiment of FIG. 2A, omitting the basket, to show the shaft, sheath, and filaments that make up the basket loops;

FIG. 3 shows a sectional side view, taken along line 3-3 of FIG. 2A, of the embodiment of FIG. 2A, omitting most of the shaft in order to detail the distal and proximal ends of the instrument;

FIG. 7A shows longitudinal section view of a shaft embodiment where the jacket fills the interstitial spaces among filaments, thereby creating a substantially solid filamentous shaft;

FIG. 7B shows a cross-section, taken along line 7B-7B of FIG. 7A, of the shaft embodiment of FIG. 7A;

FIG. 8 shows a side view of an embodiment configured as a video-guided guidewire with an integral imaging system;

FIG. 9 shows a perspective view of the imaging system of the embodiment of FIG. 8;

FIG. 10 shows a sectional view of the imaging system of the embodiment of FIG. 8;

FIG. 11A shows a side view of an embodiment configured as a video-guided, steerable retrieval device;

FIG. 11B shows a partial perspective view of an alternative embodiment of the shaft and sheath assembly, wherein the imaging and illuminations systems are contained in an inner wall of the sheath, so as to maintain a substantially constant cross-sectional area along the length of the sheath-shaft assembly;

FIG. 12 shows a sectional view of the imaging system of the embodiment of FIG. 11A;

FIG. 13 shows a front-perspective view of the distal end of the embodiment of FIG. 11A, highlighting the functional element, in this case a retrieval basket;

FIG. 14 shows a back-perspective view of the distal end of the embodiment of FIG. 11A;

FIG. 15 shows a side-perspective view of an endoscopic instrument according to the present invention;

FIG. 16 shows a detail view of the distal end of the embodiment of FIG. 15; and

FIG. 17 shows a longitudinal sectional view of the embodiment of FIG. 15.

DETAILED DESCRIPTION OF THE INVENTION

Figure 1A:
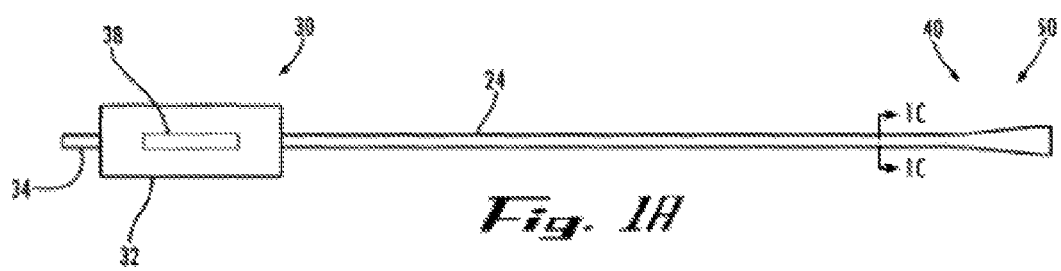
FIG. 1A shows a side view of an embodiment of an endoscopic instrument according to the present invention, in a straight configuration.

In certain aspects, the present invention relates to medical or surgical instruments, devices, or tools for minimally invasive procedures. Such devices include, but are not limited to, endoscopes, guidewires, and retrieval devices. In particular, the present invention provides novel instruments, devices, or tools based on a filamentous shaft that supports an electronic imaging system adapted to acquire an image in a restricted space, such as an internal body cavity or interstitial space. The construction and arrangement of such filamentous shafts are detailed below.

In certain embodiments, an endoscopic instrument according to the present invention comprises a flexible filamentous shaft comprising one or more filaments. In certain embodiments, the shaft may be encased in a jacket that serves to bind together the filaments into a coherent filamentous core. In some embodiments, a shaft or jacketed shaft may be encased in a sheath. In some embodiments, the shaft may be slideably disposed in the sheath. Embodiments comprising a shaft and a imaging system may serve as video-guided guidewires, as noted elsewhere. Principles of guidewire construction and design considerations are well known to persons skilled in the art. For example, see U.S. Pat. No. 4,925,445, which discloses general guidewire design principles—and more specifically, guidewires made of super-elastic metallic materials; U.S. Pat. No. 5,607,419, which discloses guidewires encasing an optical fiber for delivering ultraviolet radiation from its distal end; and U.S. provisional application No. 60/561,957, titled "PLATFORM DUAL FLOPPY GUIDEWIRE, filed Apr. 13, 2004, and listing one of the inventors of the present application and co-owned by the applicant hereto.

A filamentous shaft may include accessory elements such as power conductors, signal conductors, movement control mechanisms, devices, or structures, for moderating characteristics of the shaft like stiffness or circumference, and other similar means.

A filamentous shaft may be surrounded a jacket, which serves to bind the various filaments together into a mechanically cohesive unit. The jacket can provide additional characteristics to the device, such as functioning as an insulator or providing a lubricious external surface for facilitating surgical insertion or patient comfort. It might also have biological effects, such as supporting a therapeutic agent or inhibiting microbial growth.

A filamentous shaft or jacketed filamentous shaft may be disposed in a sheath, which provides a protective outer covering, among other things. The shaft may be slideably disposed in the sheath. Like the jacket, the sheath may provide additional characteristics to the device, such providing a lubricious external surface for facilitating surgical insertion or patient comfort. It might also have biological effects, such as supporting a therapeutic agent or inhibiting microbial growth In certain embodiments, the sheath is a flexible, biocompatible polymer. For example, the sheath may be constructed from Polimide, Polyurathane, Nylon, Pebax, or Pellathane, alone or in combination. For many applications, the sheath will have a homogeneous constitution along its length, such as provided by forming the sheath in known extrusion processes. From the teachings herein, persons skilled in the art will readily recognize that sheaths may be selected or designed so as not to interfere substantially with the mechanical properties and functionality of the shaft, which may include pushability or steerability.

Alternatively, the sheath may have heterogeneous constitution. For example, it may be constructed of a blend of polymers or include structures that affect its use and performance. For example, the shaft may incorporate reinforcement fibers or have varying thickness along its length or in selected portions.

In other embodiments, an instrument according to the present invention includes a functional element disposed at the distal end of the shaft, where the functional element is a device or tool that performs a useful action or procedure within the patient's body. Representative functional elements include retrieval baskets, graspers, forceps, cautery loops, ablation devices, laser fibers (for example, for lithotripsy), and similar tools. Such embodiments may serve as, for example, a self-contained, reduced-diameter, video-guided endoscopic instrument for retrieving foreign objects or tissue samples from a patient's body.

For deflection, such embodiments may rely on the stiffness/flexibility of the shaft, which may vary lengthwise as mentioned previously. Such embodiments may further provide one or more filaments to provide active deflection of the shaft or sheath, for example, by a pull-wire controlled by a user through a mechanism in, for example, a proximal handle for the instrument. FIGS. 2A, 2B, 11, 12, 13, and show representative embodiments of this type.

Filamentous Shaft

Referring also to FIG. 3, shaft 22 comprises one or more structural filaments supporting an imaging system 50, functional element 44, or both. Optionally, the filamentous shaft may include one or more wires or filaments that provide certain functionality, such as, but not limited to, deflection filaments 26, functional-element filaments 64, signal conductors 66, power conductors 67, light conductors 68, and stiffening filaments 69. To reduce diameter, the designer of an endoscopic instrument according the present invention may select the essential filaments, in order to reduce the size and number of filaments in shaft 22. Using a battery-operated and/or wireless imaging system, for example, may eliminate power conductor 67, signal conductor. Similarly, multiplexing a combination of electrical power, control signals, and data signals on a single conductor eliminates the physical distinction between signal conductors 66 and power conductors 68. Similarly, using the patient's body as an electrical "ground" may eliminate the need to supply distinct "hot" and "ground" conductors in a signal conductor 66, power conductor 67, signal conductors 66, or both. Similarly, relying on the flexibility and stiffness of the shaft may eliminate the need for deflection filaments 26.

For clarity, the figures depict a generalized embodiment that provides a full complement of filaments, each with a distinct function. It is understood, however, that omitting filaments is a key strategy for reducing shaft diameter. Again, as persons skilled in the art will appreciate from this disclosure, an embodiment may employ only the filaments necessary to its particular purpose and may omit all other filaments in order to minimize the cross-sectional area of shaft 22. It is understood that a given filament may perform more than one role within the shaft. For example, a power conductor may also carry electronic signals and contribute to the desired degree of structural stiffness or integrity.

In some embodiments, shaft 22 further comprises a jacket 28 surrounding the various filaments to hold them together as a coherent unit, to protect the various filaments, to provide a smooth outer surface for the shaft, to provide a substrate for treatments such as lubricants, and to provide a support for imaging system 50 and other distal components.

As shown in FIGS. 1A and 2A, proximal end of shaft 22 or sheath 24 may be connected to handle 32 so that each filament can pass from handle 32 to shaft 22 and through shaft 22 to the operative destination of the filament. In some embodiments, shaft 22 is detachable from handle 32. In disposable embodiments, the handle may be physically cut away after the endoscopic instrument reaches the site of interest. And some embodiments simply omit handle 32, so that electrical or electronic filaments terminate in a connector and deflection filaments 62, functional-element filaments 64, and similar sliding actuators project from the proximal end of the shaft to permit operation of the actuated device.

Filaments

"Filament" herein refers to any extended, linear, continuous, connecting element or member, such as a wire, fiber, cable, thread, or other such substantially solid element. Each filament provides desired structural and functional characteristics. Typical filaments include single or multiple wires to conduct electrical power, electronic signals, or both; fiber optics or fiber-optic bundles to conduct light as an illumination source for imaging or as a means for conducting electronic signals; pull wires to communicate mechanical motions from one point to another; and stiffeners or similar filaments selected for desirable uniform or variable mechanical properties.

The typical materials and fabrication methods for a filament depends on its particular purpose. Filaments designed to conduct power or signals are typically fabricated from copper, aluminum, silver, gold, or other metals or alloys thereof and have an electrically insulating coating; and multiple such filaments are often bound together as a functional unit that operates as a single filament comprising multiple secondary filaments, electrically insulated from each other and (often) encased in an electrically insulating sleeve.

A deflectable shaft may be made with filaments that act as pull wires, fabricated from, for example, stainless steel, Nitinol, or a similar material selected for the proper balance of tensionablity and flexibility. Fiber optics are typically fabricated from glass fibers that are adapted to carry light from one point to another. A single fiber-optic strand can carry a large amount of data; and multiple fiber-optic strands, usually bundled together as a functional unit that acts as a single filament, can act as an illumination source or as an image-transmission system. The materials, fabrication, and utility of other sorts of filaments are discussed elsewhere, when describing a particular filament.

A filament may comprise more than one secondary filaments bound together as a functional unit. For example, a filament that conducts electrical power or an electronic signal may encompass distinct "hot" and "neutral" conductors, electrically insulated from each other, perhaps mechanically bound together by an insulating sleeve, and perhaps coaxially arranged. As mentioned, multiplexing provides a strategy for carrying both power and signals on the same wire or pair of wires, reducing the total number of filaments in the sheath.

Many filaments are round in cross-section. Non-circular, polygonal, or irregular cross-sectional shapes are within the scope of the present invention. For example, light conductors such as fiber-optic bundles may have almost any cross-section. Filaments that lend themselves to fabrication in arbitrary cross-sections can beneficially fill "leftover" spaces within the shaft such as the interstices between other adjacent filaments. For example, a light conductor packed into an otherwise empty space can increase light output without increasing the diameter of the shaft. Many filaments have an unchanging cross-sectional area and shape over the entire length of the filament. Filaments that vary lengthwise in cross-sectional area, shape, or both are within the scope of the present invention.

A filament, or a group of filaments, may have a surrounding sleeve 61 isolating the filament or group of filaments from neighboring filaments or groups of filaments. A deflection filament 66, for example, may be a pull wire with a surrounding sleeve that has a slippery inner surface in order to provide a channel for the wire; to lubricate its sliding motion; to prevent the wire from kinking into a gap within the shaft when pushed; and in general to efficiently direct the pushing or pulling motion from the actuator to the point of actuation.

Jacket

A filamentous shaft comprises one or more filaments. To integrate multiple filaments into a single unit, shaft 22 in some embodiments further comprises a jacket 28. The term "jacket" herein refers to a tubular or enveloping coating, wrapping, binding, enclosure, or similar structure that tightly surrounds or encapsulates the various filaments to bind the filaments as a mechanically coherent unit, referred to as a filament core 60. In various embodiments, a jacket may be a tube-like covering that binds core 60 into a substantially tight assembly; a tube-like structure that carries one or more filaments inside the jacket wall; a flexible rod-like member encapsulating one or more filaments; or a binding wrapped over filament core 60. Finally, certain embodiments of shaft 22 omit jacket 28.

Any material, or combination of materials, may be used to construct the jacket. Contemplated jacket materials include Polimide, Polyurathane, Nylon, Pebax, or Pellathane, latex, or other rubber; silicone or another synthetic gel; plastic or other polymer, whether alone, alloyed, or in combination. A jacket also can contain a stiff internal lattice or webbing made from metal, carbon fiber, stiff plastic, or other similar material to provide additional strength and rigidity. In some embodiments, the jacket is a thread, strap, or band of flexible polymer helically wrapped around the underlying shaft.

In certain embodiments, the aforementioned jackets may have a wall thickness sufficient to carry the imaging or illumination systems described herein. For example, referring to FIGS. 5A and 5B, jacket 128 has a channel 26 along its length that carries the imaging system for use with the shaft. The distal end of the channel includes the imaging system. The system comprises image sensor and optical elements for focusing an image on the sensor. The channels also include one or more electrical conduits that are operatively coupled to the imaging system and proximally extend therefrom. The conduits may be used to provide power to the system and communicate signals between the system and other electronic components.

In general, shaft 22 must be stiff enough to push into the patient, yet flexible enough to maneuver through bodily passages. Increasing stiffness typically makes it easier to push and control the endoscopic instrument 20, while increasing flexibility reduces trauma to the patient. The proper balance of mechanical properties depends on the particular purpose of the instrument. For instance, in tortuous anatomy, more flexibility at the distal portion is desirable; in straighter, tight passages, more rigidity is desirable. To achieve the desired properties, some embodiments of filament core 60 may include one or more stiffening filaments 69, typically a wire or similar filament selected to modify the mechanical properties of shaft 22. For example, stiffening filament 69 may be one or more stainless-steel wires included in core 60. The stiffness of shaft 22 may vary along its length, according to the particular purpose of instrument 20.

In some embodiments, jacket 28, 128, 228 additionally comprises coverings or coatings such as, but not limited to, hydrophilic or PTFE coatings to facilitate navigation through anatomy. The construction of such shafts can be based on principles of guidewire construction, which are known to persons skilled in the art.

Sheath

A sheath is a covering that, in some embodiments, surrounds a shaft or a jacketed shaft. In general, the term "sheath" refers to a tubular or enveloping coating, wrapping, binding, enclosure, or similar structure that tightly surrounds or encapsulates the shaft or jacketed shaft.

Typically, the shaft or jacketed shaft is slideably disposed within the sheath, so that the outer surface of the shaft or jacketed shaft slides lengthwise within the sheath.

In various embodiments, a sheath may be a tube-like covering surrounding the shaft; a tube-like structure that carries one or more filaments inside the sheath wall; or a binding wrapped over the shaft or jacketed shaft. Finally, certain embodiments of the shaft omit sheath 24.

The materials, or combination of materials, for sheaths are similar to those used for jackets. As such, contemplated sheath materials include Polimide, Polyurathane, Nylon, Pebax, or Pellathane, latex, or other rubber; silicone or another synthetic gel; plastic or other polymer, whether alone, alloyed, or in combination. Like a jacket, a sheath also can contain a stiff internal lattice or webbing made from metal, carbon fiber, stiff plastic, or other similar material to provide additional strength and rigidity. In some embodiments, the sheath is a thread, strap, or band of flexible polymer helically wrapped around the underlying shaft or jacketed shaft.

In certain embodiments, the sheath may have a wall thickness sufficient to carry thereon the imaging or illumination systems or conduits, or pull wires, described elsewhere.

In certain embodiments, sheath 24 additionally comprises coverings or coatings such as, but not limited to, hydrophilic or PTFE coatings to facilitate navigation through anatomy. The construction of such sheaths can be based on known guidewire construction principles.

Shaft Embodiments

Figure 4B:
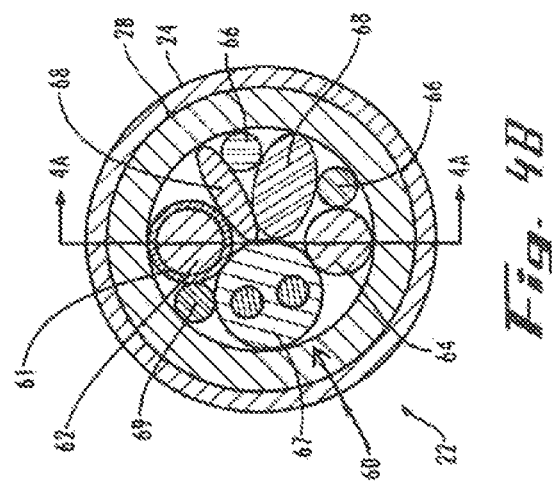
FIG. 4B shows a cross-section, taken along line 4B-4B of FIG. 4A, of the shaft embodiment of FIG. 4A.
Figure 4A:
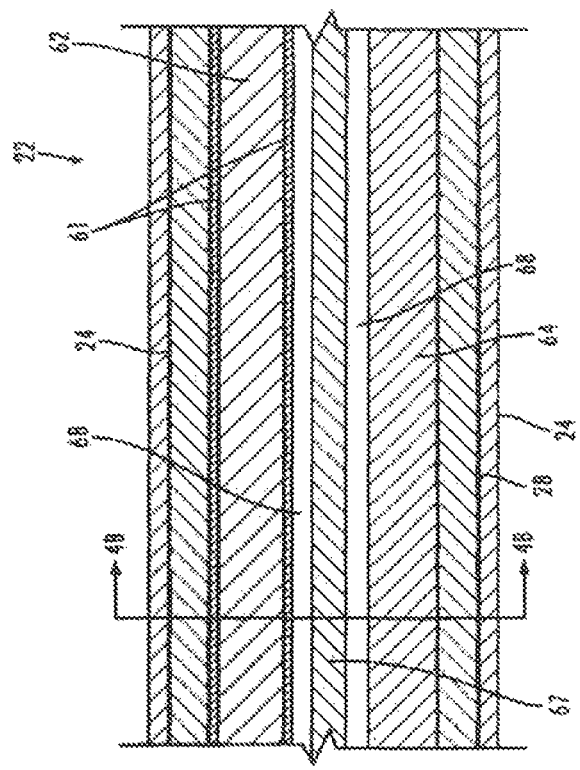
FIG. 4A shows a longitudinal sectional view, taken along line 4A-4A of FIG. 4B, of a shaft embodiment, where the shaft comprises a filamentous core surrounded by a jacket.

FIGS. 4A and 4B depict a shaft embodiment comprising a filament core 60 and a jacket 28. A sheath 24 is, slideably disposed over jacket 28. Jacket 28 is a thin-walled tube-like covering that forms an exterior wall of filament core 60 to bind core 60 into a substantially tight assembly, and provide a supporting structure for imaging system 50 and other distal components of endoscopic instrument 20. Filaments at the outer perimeter of core 60 contact the inner wall of jacket 28, and adjacent filaments contact each other lengthwise along shaft 22, so that core 60 is bundle within jacket 28. Because many filaments have hard, fixed crosssectional profiles, filaments that are pressed into contact may nonetheless leave open spaces or interstices among themselves. Typically, such gaps run lengthwise within core 60, as best shown in cross-section in FIG. 4B.

Sleeve 24 is a tube-like structure tightly over jacket 28. Outer wall of jacket 28 slides longitudinally within sheath 24. A typical material for sheath 24 of this type is extruded polymer of construction known in the art. Sheath 24 may be fabricated as a pre-formed tube with core 60 inserted therewithin to assemble shaft 22. Alternatively, sheath 24 may be applied as a sheet wrapped around core 60 and then fused edge-to-edge lengthwise to form a tube, for example, by any of various adhesives or welding techniques known in the art.

In FIG. 4B, power conductor 67 comprises two parallel or coaxial conductors, illustrating a compound filament structure mentioned elsewhere. The conductors may be contained in an electrically insulating sleeve or jacket. As also mentioned, deflecting filament 62 slides within a sleeve 61 that has a slippery inner surface, facilitating the push-pull operation of filament 62. Sleeve 61 is typically an extruded polymer tube similar to sheath 24. As depicted, light conductor 68 has a non-circular profile, to make efficient use of the interstitial space defined by neighboring filaments 62, 67, 68, and 66.

Figure 5A:
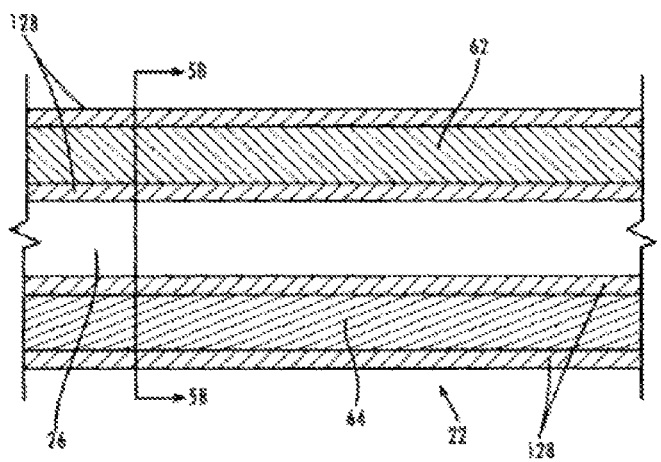
FIG. 5A shows a longitudinal sectional view, taken along line 5A-5A of FIG. 5B, of another shaft embodiment, where filaments reside in the sheath wall.
Figure 5B:
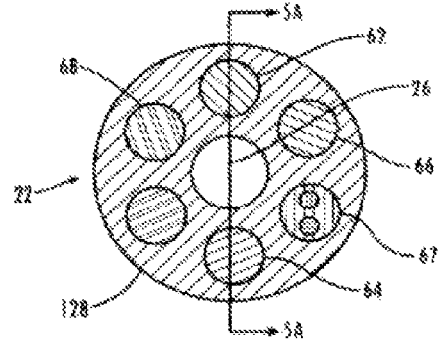
FIG. 5B shows a cross-section, taken along line 5B-5B of FIG. 5A, of the shaft embodiment of FIG. 5A.

Referring especially to FIGS. 5A and 5B, in certain embodiments, shaft 22 comprises plurality of filaments 62, 64, 66, 67, and 68 encased in a jacket 128 configured as a tube-like structure that carries one or more filaments inside the wall of jacket 128, possibly leaving one or more working channels 26 running all or part of the length of shaft 22. In contrast to the embodiment of FIGS. 4A and 4B, the embodiment of FIGS. 5A and 5B does not have a sheath, so that the external surface of jacket 128 is in contact with the patient. When jacket 128 forms the external surface of the shaft, hydrophilic or other coatings applied to jacket 128 may improve patient comfort or the ease of use of the endoscopic instrument.

Channel 26, if present, provides a means for passing tools or treatments down shaft 22 to distal end 40 inside the patient. The proximal end of channel 26 terminates in an opening (not shown) in handle 32 or shaft 22 in order to allow insertion of tools or treatments. The distal end of working channel 26 similarly terminates in an opening (not shown) a the distal end 40 or thereabouts of shaft 22.

Figure 6A:
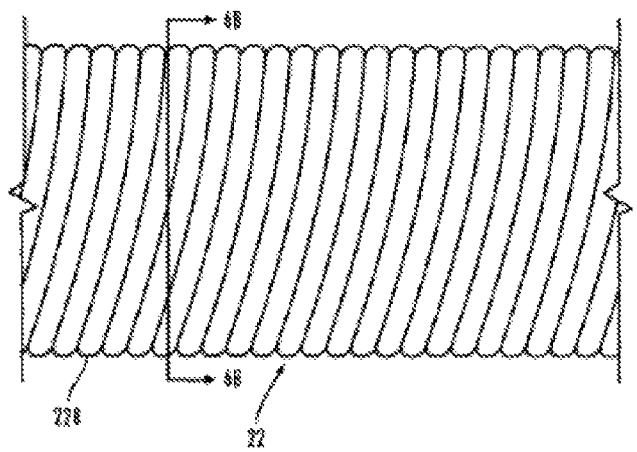
FIG. 6A shows a longitudinal view of another shaft embodiment, wherein the jacket is a wrapping applied to a filamentous core.
Figure 6B:
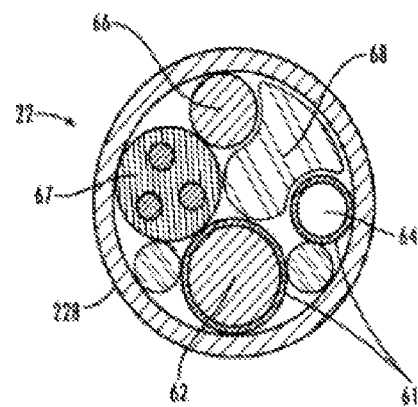
FIG. 6B shows a cross-section, taken along line 6B-6B of FIG. 6A, of the shaft embodiment of FIG. 6A.
Figure 12:
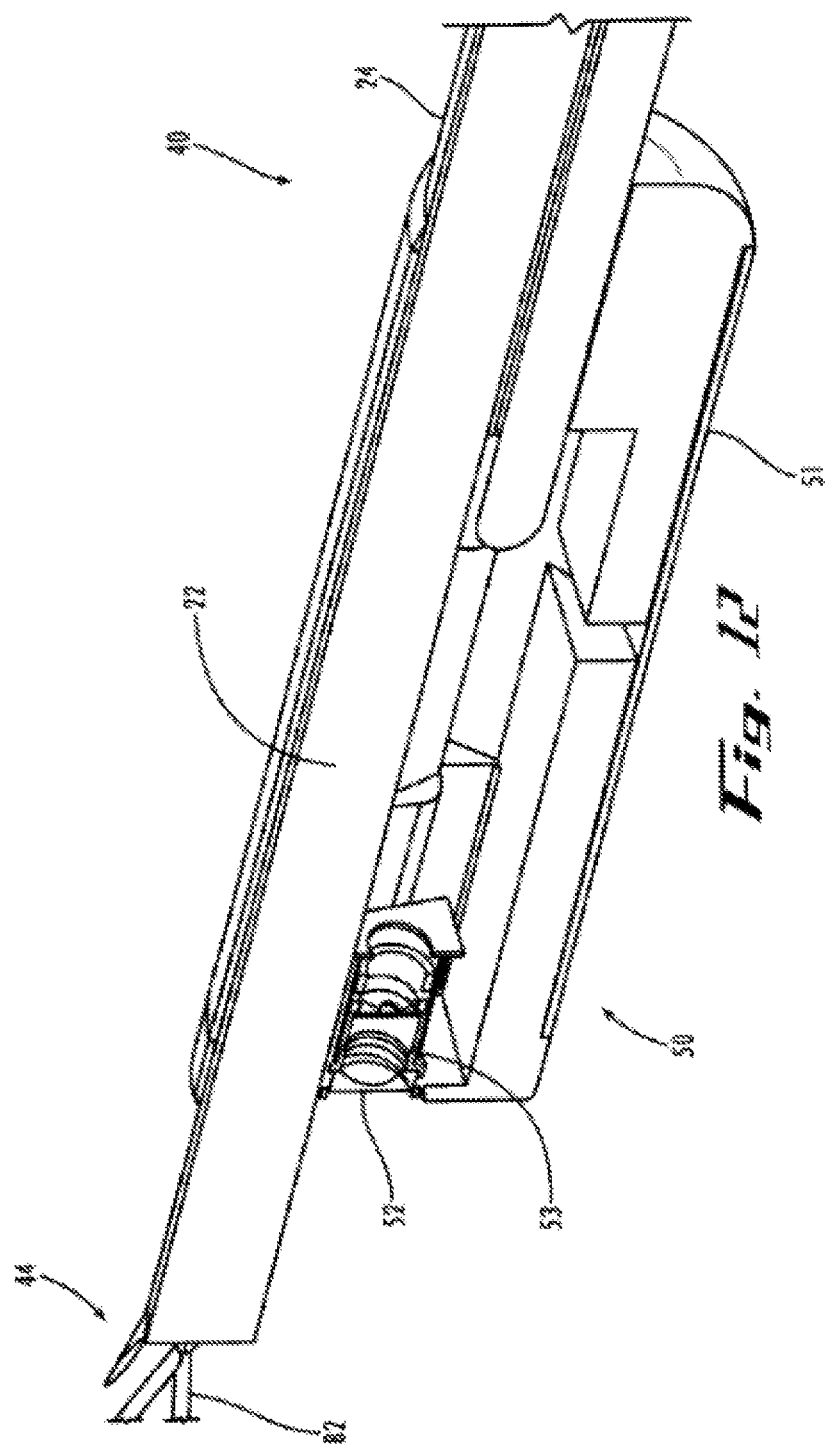
Figure 13:
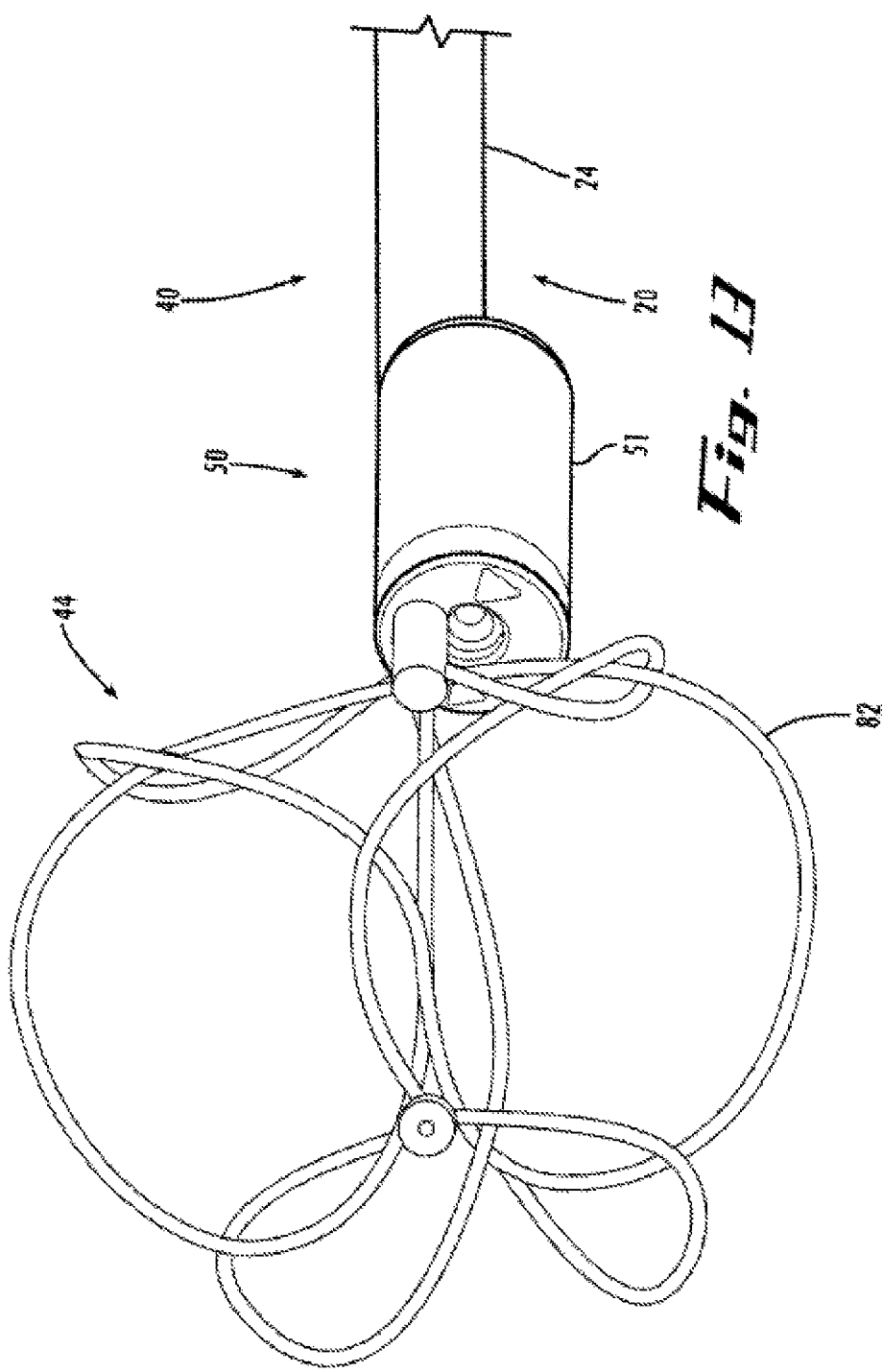
Figure 14:
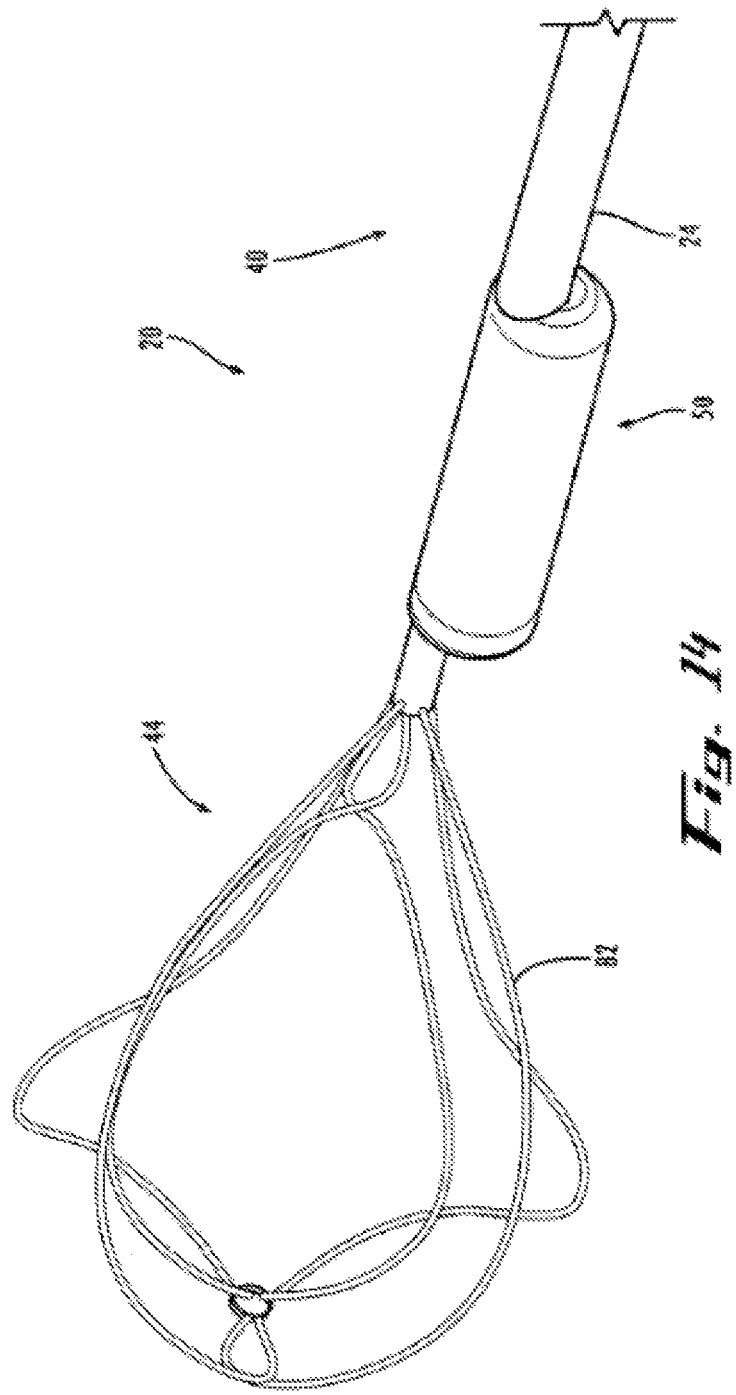

Referring to especially FIGS. 6A and 6B, in certain embodiments, jacket 28 is a flexible filament helically wrapped over filament core 60 to bundle the filaments together and to provide a substantially smooth outer surface. For example, jacket 28 may be a smooth or flat wire tightly wrapped around core 60. Suitable materials for jacket 28 include Nitinol and stainless steel, as persons skilled in the art will appreciate.

Figure 7:
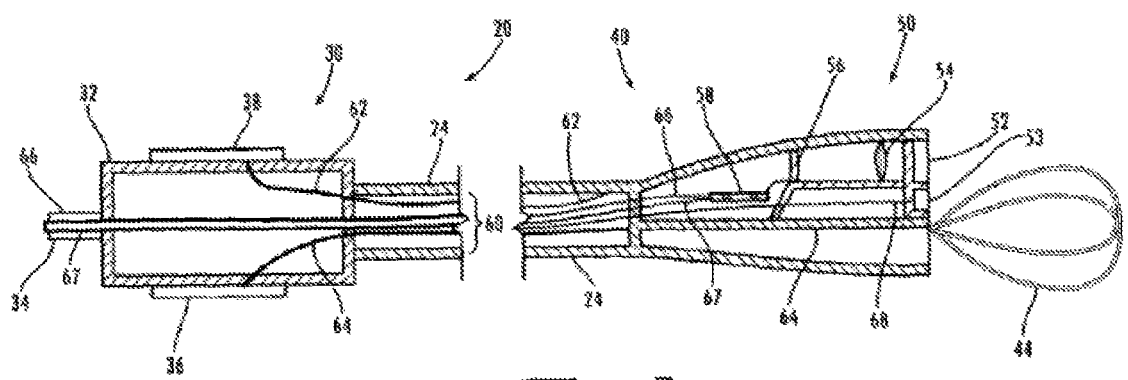

Referring especially to FIGS. 7A and 7B, in certain embodiments, jacket 328 is a flexible rod-like member encapsulating one or more filaments, so that the sheath material in general fills the interstices between filaments. Jacket 328 may be fabricated by molding, for example, or by dipping filament core 60 in a liquid plastic material that flows among the filaments to form a substantially solid rod surrounding the filaments; or by any of other methods known in the art. The embodiment of FIGS. 7A and 7B has a sheath 24 slideably disposed over the sheath.

Channels and Other Features

"Channel" herein refers to a lumen running all or part of the length of the shaft or sheath, for example, to support the imaging system or a functional element. The sheath may include other channels, including a channel for a solid-state lighting illumination system. For example, one or more LED lights may be disposed at the distal end of a channel and conduits for powering the LEDs extend proximally therefrom. Alternatively, LEDs could be located at a proximal portion of the sheath, or outside the sheath, and be optically coupled to one or more fibers disposed in the channel, which emit light from the distal end into a target site. As a further example, the sheath may include a working channel for inserting another device, such as a laser fiber for ablation or a surgical instrument. Still other channels may be used for suction; irrigation; introduction of therapeutic agents or other substances into a target site; filaments for deflecting the shaft (described in more detail elsewhere below).

In certain embodiments, the sheath includes one or more pull filaments, such as wires connected to a distal end portion that travels down the length of the sheath to a handle disposed on the distal end of the sheath. There, the filaments connect to a handle having a slide, trigger, dial, or other control mechanism that can be actuated to pull and filaments and deflect the sheath and the shaft housed therein.

A filamentous shaft and associated imaging system in accordance with the teachings herein may support various uses and function. For example, it may be used in an assembly of a guidewire and guided instrument or device. The guided instrument or device may be a catheter or a stent, for example. The shaft also can include at its distal end a functional element an optional retrieval system for dislodging or removing tissue, obstructions, artifacts, or other items from a patient's body. The retrieval system can be a set of biopsy forceps; a basket or other enclosure; a wire loop or snare; a suction tube or funnel; or other similar device.

Figure 1B:
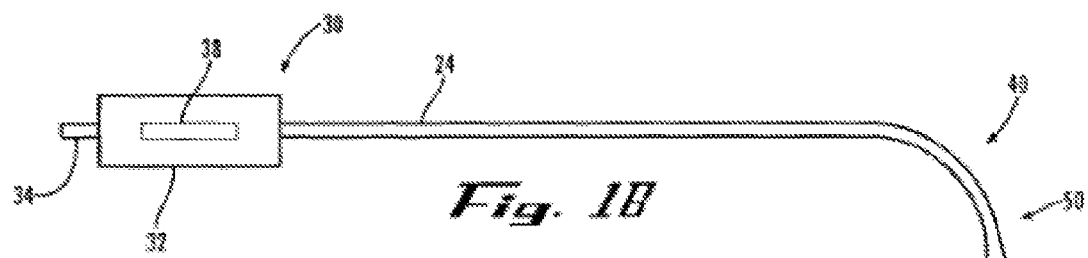
FIG. 1B shows a side view of the embodiment of FIG. 1A in a deflected configuration.
Figure 1C:
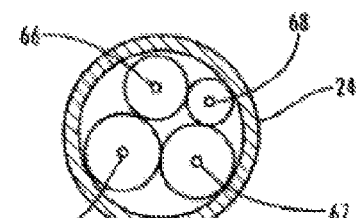
FIG. 1C shows a cross-section taken along the line 1C-1C in FIG. 1A.

Some embodiments of the present invention contemplate the use of a passive shaft—that is, one that has no active provision for directional control. Other embodiments contemplate the use of a deflecting shaft—that is, one that includes a mechanism for actively bending the distal end 40 of shaft 22, for example, as shown in FIG. 1B. Direction-control element 62 provides a means of introducing deflection. In some embodiments, directional-control element 62 comprises one or more pullable wires carried on shaft 22. The distal end of a pull wire is affixed to shaft 22 at or near its distal end. The proximal end of the pull wire is affixed to an actuator at or near handle 32. One example of an actuator is a slide mechanism operatively coupled to a wire or group of wires. Moving the slide enables a positive and consistent deflection of the distal end of instrument 20 as shown in FIG. 1B. The mechanism may include markings, detents, locks, and other means for controlling the degree of deflection.

Because imaging system 50 is affixed to the distal end of shaft 22, controllably deflecting distal end 40, thereby controllably changing positioning of functional elements at the distal end.

Electronic Imaging and Illumination Systems

Imaging system 50 comprises at least one imaging sensor 56 together with optical, illumination, and control components. A filamentous shaft according to the present invention provides mechanical, structural, electrical, and electronic support for the imaging and illumination systems. For example, embodiments of imaging system 50 that rely on an external power supply receive electrical power through a power conductor 67 that passes through shaft 22, typically terminating at a connector at the proximal end. In other embodiments, imaging system 50 may be battery operated, eliminating power conductor 67.

Referring to FIG. 3, a typical imaging system 50 comprises optical face 52, image transmitting element 54, an imaging device 56, and supporting electronics and conductors. Optical face 52 is an optically transparent view port that may be omitted in some embodiments of imaging system 50, which rely on the distal-most optical element to seal imaging system 50. Imaging transmitting element 54 is an optical system, typically but not necessarily comprising one or more lenses, that projects an image from the site of interest to imaging device 56. Image transmitting element 54 may be a fixed focus or focusable system. Imaging sensor 56 is a Charge Coupled Device (CCD) chip, Complementary Metal Oxide Semiconductor (CMOS) chip, or other device capable of translating an optical image into an analog or digital signal.

Control system 58 represents electronic devices not built into imaging sensor 56 but which may be required to control the operation of imaging sensor 56 or other functional components of imaging system 50. Current imaging devices typically require off-chip image processing, control interfaces, and other supporting electronics depicted as control system 58. Such functions may be included in devices situated elsewhere, however. Improved imaging devices that combine these functions in one or more physical parts are within the scope of the present invention.

Referring especially to FIGS. 8, 9, and 10, in some embodiments, imaging system 50 is housed in a capsule-like housing disposed at distal end of shaft 22. In such embodiments, when the physician passes the capsule into the patient, the orifice or incision temporarily dilates to accommodate the diameter of the capsule. After the capsule passes deeper into the patient toward the site of interest, the orifice or incision relaxes to accommodate the smaller diameter of shaft 22, jacket 28, or sheath 24. Minimizing capsule diameter, shaft diameter, or both limits the amount and duration of the stretching and pressure imposed on patient tissues.

Figure 15:
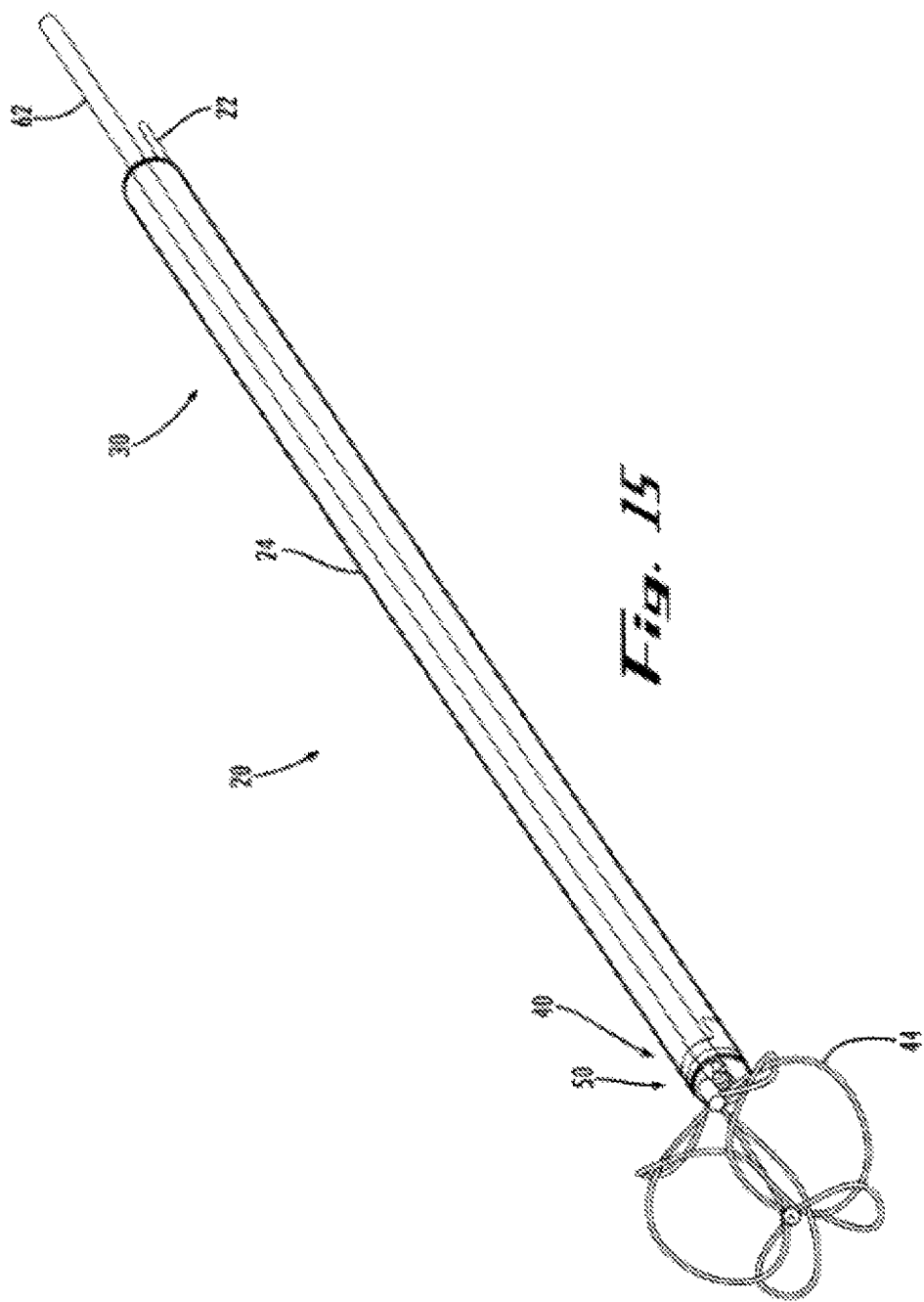
Figure 16:
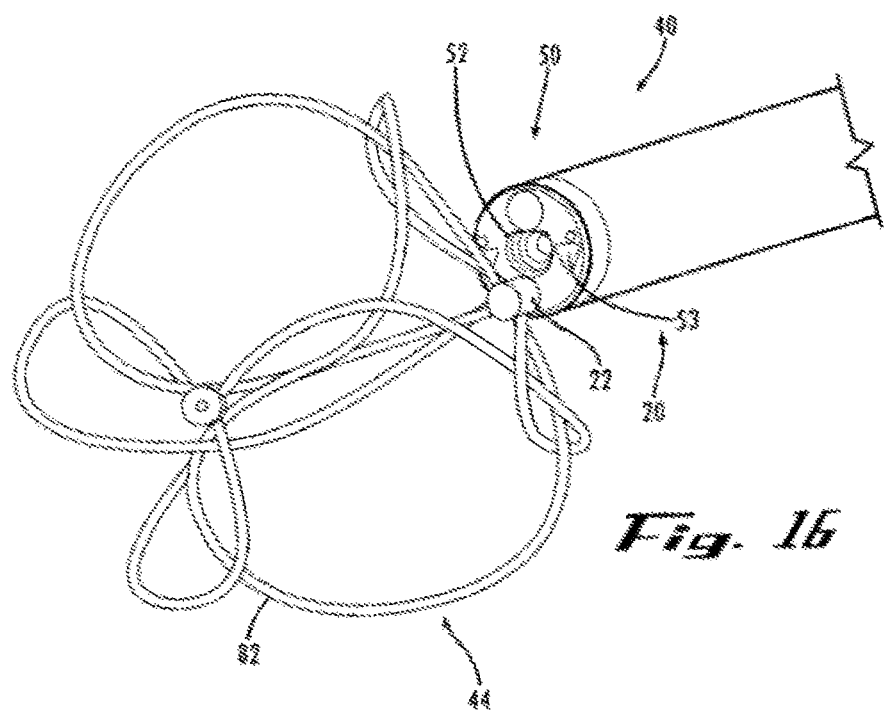
Figure 17:
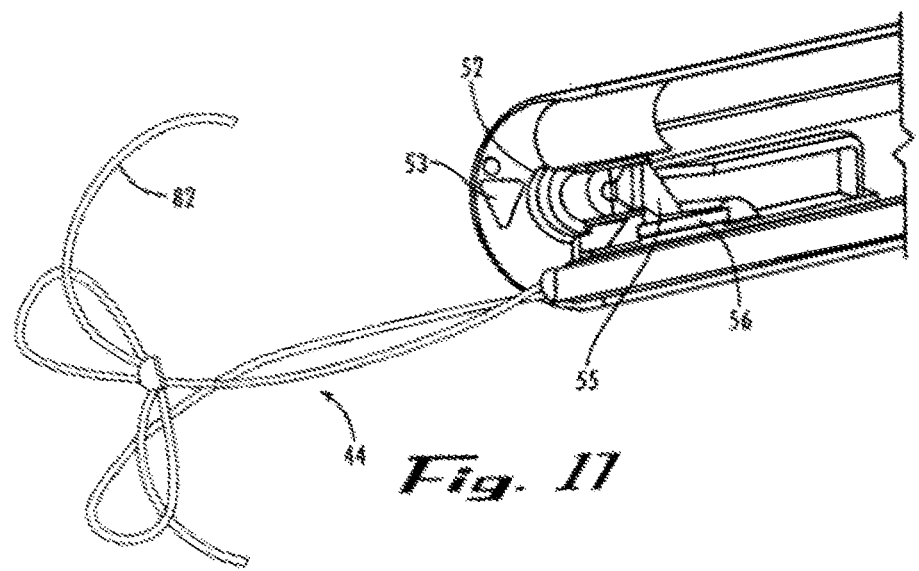

Referring especially to FIGS. 15, 16, and 17, other embodiments place the imaging system within the distal end of the endoscopic instrument, rendering capsule 51 unnecessary. Such embodiments reduce or eliminate the joint between the shaft and the imaging system, thereby reducing mechanical discontinuity and permitting coverings or coatings to extend without interruption to the distal end of the endoscope. Furthermore, such embodiments beneficially minimize the diameter of imaging system 50 to approach or equal that of the filamentous shaft. Eliminating capsule 51 facilitates using the endoscopic instrument to act as, for example, a video-guided guidewire. In such embodiments, the physician uses the imaging system to find a site of interest, slips a catheter (for example) over the device, advances the catheter over the guidewire to the site of interest, and then withdraws the guidewire, leaving the catheter in place.

Representative video chip technology usable in this device is disclosed in U.S. Pat. No. 6,659,940, issued Dec. 9, 2003 and titled "IMAGE SENSOR AND AN ENDOSCOPE USING THE SAME"; and also disclosed in international patent application number PCT/IL03/00399 (U.S. application Ser. No. 10/514,604), titled MINIATURE CAMERA HEAD, filed Nov. 16, 2004; these applications are hereby incorporated by reference in their entirety for all purposes. Among other things, these patent documents disclose compact electronic imaging systems suitable for use in medical instruments, including imaging systems with the imaging surface oriented non-perpendicularly to the optical axis of the shaft and the use of solid-state lighting systems with light sources disposed at the distal end of an endoscope.

Functional Elements

Functional elements include various devices for performing procedures on an object or tissue at a target site in the patient's body. For example, the functional element may be used for grasping retrieving objects such as foreign bodies or stones (calculi) from the patient's body; or it may be used for cutting and retrieving polyps or biopsy samples. Contemplated functional element devices include retrieval baskets, biopsy forceps, suction devices, electrosurgical devices, laser devices, and ablation devices. FIGS. 11 through 16 show representative embodiments of an endoscopic instrument according to the present invention including a retrieval basket as a functional element.

Examples of filamentous shafts, retrieval baskets, and handle-based control mechanisms, but without associated imaging systems, are disclosed in international patent application number PCT/US0209531 (U.S. application Ser. No. 10/013,005), titled "RETRIEVAL BASKET FORA SURGICAL DEVICE AND SYSTEM AND METHOD FOR MANUFACTURING SAME," the disclosure of which is hereby incorporated by reference in its entirety for all purposes.

Proximal End

Endoscopic instrument 20 comprises a proximal end 30, a shaft 22, and a distal end 40. In certain embodiments, such as that shown in FIGS. 1A and 1B, proximal end 30 comprises a handle 32, a connector 34, and a deflection actuator 38. The proximal end of handle 32 is affixed to the distal end of shaft 22 so that pull wires, conductors, and other filaments have an operative connection from handle 32 to shaft 22. Handle 32 is sized and shaped for manipulation by the operator and is typically fabricated from, for example, metal, plastic, thermoplastic, or other materials known in the art, alone or in combination, selected for properties such as strength, cost, and the ability to form complex shapes.

The proximal end of handle 32, when present, is affixed to the distal end of shaft 22 so that pull wires, conductors, and other filaments are operatively connected from handle 32 to shaft 22. In certain embodiments, handle 32 provides a means for facilitating passing a catheter, stent, or a similar device over shaft 22 in order to emplace the device at the site of interest in the body. For example, handle 32 may be adapted to be removed from shaft 22, or even cut off from it in a disposable instrument, thereby eliminating handle 32 as an obstruction to emplacing a catheter. In an alternative embodiment, shaft 22 is provided in a length sufficient to slip the device over shaft 22 prior to inserting shaft 22 into the patient. With this arrangement, the catheter (for example) remains outside the patient until distal end 40 reaches the site of interest, when the physician passes the catheter over the external portion of shaft 22 and into the patient over the internal portion of shaft 22.

Handle 32 provides a support for connector 34, which provides a means for passing electrical power and control signals into endoscopic instrument 20 and for passing image data and other data from instrument 20 to external equipment (not shown), for example, to display the acquired image.

Handle 32 further supplies a support for controls such as deflection actuator 38. Referring also to FIG. 3, deflection actuator 38 is a means for controlling the angular deflection of distal end 40. Actuator 38 typically comprises one or more levers, slides, triggers, or similar controls, each attached to at least one deflection filament 62, typically a pull wire or other means for communicating motion from actuator 38 to the distal end of shaft 22. Extending or retracting actuator 38 pushes or pulls filament 62, which slideably extends lengthwise thorough shaft 22 to a point of attachment toward the distal end 40 of shaft 22. Actuator 38 and filament 62 together provide a means for controllably bending shaft 22 at its distal end 40 or thereabouts, thereby changing the angle of the shaft tip and imaging system 50 with respect to the longitudinal axis of handle 32 and the proximal end of shaft 22. Changing the deflection of distal end 40 while pressing instrument 20 into the patient allows the physician to steer instrument 20 within the patient's body.

A single actuator 38 and corresponding deflection filament 62 deflect the shaft in one axis, but rotating handle 32 also rotates distal end 40, so that one axis of deflection is sufficient to steer the instrument in any direction in the patient's body. An alternative embodiment provides two or more distinct actuators 38a through 38n, connected to corresponding distinct deflection filaments 62a through 62n, permitting multi-axis deflection without rotating handle 32. Actuator 38 may have a lock (not shown) to preserve a given amount of deflection without the need to hold actuator 38 in place. "Pull wire" herein refers to a filament or other mechanical linkage adapted to communicate motion from one point to another, by pushing, pulling, or both, and does not imply that the filament is necessarily fabricated from metal wire.

As shown in FIGS. 2A and 2B, for embodiments that further comprise a functional element 44 such as a retrieval basket, handle 32 further provides a support for functional-element actuator 36. Actuator 36 is in mechanical communication with at least one functional-element filament 64 such as a pull wire that is in turn in communication with functional element 44. The operation of functional-element actuator 36 is similar to that of directional actuator 38. Pushing, pulling, or otherwise manipulating actuator 36 activates, operates, or otherwise changes functional element 44. For example, if functional element 44 is a retrieval basket, then pushing a sliding actuator 36 might push the basket open, and pulling actuator 36 might pull the basket closed, so that the physician can ensnare and extract an object of interest. Actuator 36 may have a lock (not shown) to hold the control in a fixed position.

In certain embodiments, such as as shown in FIG. 11A, proximal end 30 omits the handle. In such embodiments, shaft 22 may project from the distal end 30, and shaft 22 may be slideably disposed within sheath 24. Manipulating proximal end 40 thus permits the physician to operate functional element 44, which is situated at the distal end of shaft 22. Pull wires may similarly project from distal end 30 of sheath 24, for example, to control deflection by manipulating the distal end of deflection filament 62. In embodiments that omit handle 32, any power conductors 67, signal conductors 68, and similar filaments may terminate in a connector situated at the distal end 30 of endoscopic instrument 20.

FIG. 11B shows a partial perspective view of an alternative embodiment of the shaft and sheath assembly, wherein the imaging and illuminations systems 50, 53 are contained in an inner wall of the sheath, so as to maintain a substantially constant cross-sectional area along the length of the sheath-shaft assembly.

Persons skilled in the art will recognize that many modifications and variations are possible in the details, materials, and arrangements of the parts and actions which have been described and illustrated in order to explain the nature of this invention and that such modifications and variations do not depart from the spirit and scope of the teachings and claims contained therein.

What is claimed:

1. A medical instrument device, comprising:
a flexible, filamentous shaft, comprising:
a) a plurality of filaments forming a filamentous core, wherein the plurality of filaments comprise:
a deflection system comprising at least one deflecting filament with a distal end portion operatively coupled to a distal end portion of the medical instrument device and proximal end operatively coupled to a proximal end portion of the medical instrument device, and a control mechanism at the proximal end portion of the medical instrument device enabling a user to pull the at least one deflecting filament and deflect the distal end portion of the deflecting filament; and
an imaging system comprising an image sensor carried on the distal portion of the medical instrument device;
b) a jacket binding the plurality of filaments together forming the filamentous core; and
c) a flexible sheath slideably disposed over the jacket;
wherein the flexible sheath has a functional element at the distal end of the medical instrument device for performing a procedure on an object or tissue at a target site in a patient's body,
wherein the at least one deflecting filament is slideably housed in a sleeve, and
wherein one or more of the plurality of filaments are in contact with an inner wall of the jacket, and the plurality of filaments being in contact with each other lengthwise along the flexible, filamentous shaft so that the filamentous core is bundled within the jacket.

2. The medical instrument device of claim 1, wherein the flexible sheath comprises a polymer tube.

3. The medical instrument device of claim 2, wherein the polymer tube has a substantially uniform composition along a majority of an insertable, distal portion of the flexible sheath.

4. The medical instrument device of claim 3, further comprising at least one solid-state illumination source disposed at the distal end of the medical instrument device.

5. The medical instrument device of claim 1, wherein the jacket has an outer diameter that closely matches an inner diameter of the flexible sheath so that an overall outer diameter of the medical instrument device is minimized.

6. The medical instrument device of claim 5, wherein an insertable portion of the sheath consists essentially of a polymer tube.

7. The medical instrument device of claim 6, wherein the functional element comprises a device for capturing or manipulating tissue or objects at a surgical site in a patient's body.

8. The medical instrument device of claim 1, wherein the functional element comprises a device that has a first configuration when disposed in the sheath and a second configuration when deployed from the distal end of the sheath.

9. The medical instrument device of claim 1, wherein the flexible, filamentous shaft includes an illumination source for emitting light from the distal end of the flexible, filamentous shaft.

10. The medial instrument device of claim 9, wherein the plurality of filaments is between 2 to 5 filaments, and at least one filament provides structural support of a predetermined rigidity and flexibility, and at least one filament of the plurality of filaments is operatively coupled to the image sensor and comprises an electrical conduit for power and/or signals.

11. The medical instrument of claim 10, wherein the image sensor comprises a CMOS image sensor.

12. The medical instrument of claim 1, wherein the image sensor has an imaging surface oriented non-perpendicularly to an optical axis of the shaft.

13. The medical instrument of claim 1, wherein the image sensor comprises a CMOS image sensor.

14. The medical instrument of claim 1, wherein the image sensor has an active imaging surface that is longer than an inner diameter of the sheath.

15. A medical instrument device, comprising:
a flexible filamentous shaft comprising:
- a) a flexible sheath comprising a polymer tube;
- b) a functional element at a distal end for performing a procedure on an object or tissue at a target site in a patient's body;
- c) a plurality of filaments forming a filamentous core, wherein the plurality of filaments comprise:
  a deflection system comprising at least one deflecting filament with a distal end portion coupled to a distal end portion of the medical instrument device and a proximal end portion coupled to a proximal end portion of the medical instrument device, and a control mechanism at the proximal end portion of the medical instrument device enabling a user to manipulate the at least one deflecting filament and deflect the distal end portion of the medical instrument device;
wherein the at least one deflecting filament is slideably housed in a sleeve,
wherein the flexible, filamentous shaft includes a jacket binding the plurality of filaments together forming the filamentous core,
wherein the filamentous core includes one or more of the plurality of filaments at an outer perimeter in contact an inner wall of the jacket, and the plurality of filaments are in contact with each other lengthwise along the flexible, filamentous shaft; and
wherein the jacket has an outer diameter that closely matches an inner diameter of the flexible sheath.

16. A medical instrument comprising:
a flexible, filamentous shaft comprising:
- i. a plurality of filaments forming a filamentous core;
- ii. the plurality of filaments including conductors operatively coupled to the image sensor so as to communicate power and signals between the sensor and a location proximal to an insertable portion of the medical instrument:
- iii. one or more of the plurality of filaments are deflecting filaments constructed and arranged to provide pushability and steerability to the medical instrument sufficient to deliver a distal end of the medical instrument to a predetermined target site in a patient's body, wherein the deflecting filaments are slideably housed in a sleeve;
- iv. a jacket binding the plurality of filaments and the sleeve forming the filamentous core, and
- v. a flexible sheath slideably disposed over the jacket;
an image sensor carried on a distal end portion of the flexible, filamentous shaft;
wherein the plurality of filaments are in contact with an inner wall of the jacket and the plurality of filaments in contact with each other lengthwise along the flexible, filamentous shaft.

17. The medical instrument of claim 16 wherein the medical instrument comprises a guidewire capable of receiving a predetermined guided device, the flexible, filamentous shaft and guidewire forming a functionally complementary assembly so as to enable delivery of the guided device to a target location in a patient's body.

18. The medical instrument of claim 17 wherein the medical instrument is adapted to deliver the guided device to a region comprising the ureter, bladder or kidney of a patient.

19. The medical instrument of claim 18 wherein the guided device comprises a catheter or stent.

20. The medical instrument of claim 17 wherein the medical instrument is adapted to deliver the guided device to a region comprising the esophageal tract or gastrointestinal tract of a patient.

* * * * *

UNITED STATES PATENT AND TRADEMARK OFFICE
CERTIFICATE OF CORRECTION

PATENT NO. : 8,517,921 B2  
APPLICATION NO. : 11/109041  
DATED : August 27, 2013  
INVENTOR(S) : Tremaglio et al.

Page 1 of 1

It is certified that error appears in the above-identified patent and that said Letters Patent is hereby corrected as shown below:

In the Claims

Claim 10, Column 18, Line 63, delete "medial" insert --medical--

Signed and Sealed this  
Twenty-second Day of October, 2013

Teresa Stanek Rea  
*Deputy Director of the United States Patent and Trademark Office*